US011147276B2

(12) United States Patent
Floro et al.

(10) Patent No.: US 11,147,276 B2
(45) Date of Patent: Oct. 19, 2021

(54) COMPOSITIONS AND METHODS FOR IMPROVING TOMATO PRODUCTION

(71) Applicant: NewLeaf Symbiotics, Inc., St. Louis, MO (US)

(72) Inventors: Rachel DiDonato Floro, St. Louis, MO (US); Justin Lee, St. Louis, MO (US); Gregg Bogosian, Clarkson Valley, MO (US); Doug Bryant, Temecula, CA (US)

(73) Assignee: NewLeaf Symbiotics, Inc., St. Louis, MO (US)

( * ) Notice: Subject to any disclaimer, the term of this patent is extended or adjusted under 35 U.S.C. 154(b) by 0 days.

(21) Appl. No.: 16/443,141

(22) Filed: Jun. 17, 2019

(65) Prior Publication Data
US 2019/0297895 A1    Oct. 3, 2019

Related U.S. Application Data

(63) Continuation of application No. 15/126,483, filed as application No. PCT/US2014/068611 on Dec. 4, 2014, now Pat. No. 10,368,547.

(60) Provisional application No. 61/954,390, filed on Mar. 17, 2014.

(51) Int. Cl.
| A01N 63/20 | (2020.01) |
| A01N 25/00 | (2006.01) |
| A01N 25/04 | (2006.01) |
| A01N 25/08 | (2006.01) |

(52) U.S. Cl.
CPC ............ *A01N 63/20* (2020.01); *A01N 25/04* (2013.01); *A01N 25/08* (2013.01)

(58) Field of Classification Search
None
See application file for complete search history.

(56) References Cited

U.S. PATENT DOCUMENTS

| 4,336,334 A | 6/1982 | Powell et al. |
| 5,106,648 A | 4/1992 | Williams |
| 5,302,525 A | 4/1994 | Groleau et al. |
| 5,403,799 A | 4/1995 | Miller et al. |
| 5,403,809 A | 4/1995 | Miller et al. |
| 5,512,069 A | 4/1996 | Holland et al. |
| 5,961,687 A | 10/1999 | Joshi et al. |
| 6,107,067 A | 8/2000 | Miller et al. |
| 6,174,837 B1 | 1/2001 | Joshi et al. |
| 6,329,320 B1 | 12/2001 | Joshi et al. |
| 7,214,509 B2 | 5/2007 | Schnoor et al. |
| 7,435,878 B2 | 10/2008 | Holland |
| 8,153,118 B2 | 4/2012 | Holland et al. |
| 8,181,388 B2 | 5/2012 | Berger |
| 8,778,660 B2 | 7/2014 | Holland et al. |
| 9,181,541 B2 | 11/2015 | Bogosian |
| 9,845,462 B2 | 12/2017 | Bogosian |
| 10,098,353 B2 | 10/2018 | Breakfield et al. |
| 10,111,438 B2 | 10/2018 | Floro et al. |
| 10,212,939 B2 | 2/2019 | Floro et al. |
| 10,287,544 B2 | 5/2019 | Bogosian |
| 10,368,547 B2 | 8/2019 | Floro et al. |
| 10,448,645 B2 | 10/2019 | Breakfield et al. |
| 10,450,556 B2 | 10/2019 | Bogosian |
| 10,757,946 B2 | 9/2020 | Allen et al. |
| 2001/0001095 A1 | 5/2001 | Joshi et al. |
| 2003/0211082 A1 | 11/2003 | Holland |
| 2005/0096225 A1 | 5/2005 | Johnson |
| 2006/0059581 A1 | 3/2006 | Spencer et al. |
| 2006/0150488 A1 | 7/2006 | Pearce et al. |
| 2006/0228797 A1 | 10/2006 | Holland et al. |
| 2007/0074451 A1 | 4/2007 | Pearce et al. |
| 2010/0093538 A1 | 4/2010 | Gnanamanickam |
| 2012/0167257 A1 | 6/2012 | Holland et al. |
| 2013/0324407 A1 | 12/2013 | Bogosian |
| 2014/0228212 A1 | 8/2014 | Pedersen et al. |
| 2015/0337256 A1 | 11/2015 | Bogosian |
| 2016/0046925 A1 | 2/2016 | Bogosian |
| 2016/0073641 A1 | 3/2016 | Allen et al. |
| 2016/0120188 A1 | 5/2016 | Bogosian |
| 2016/0295868 A1 | 10/2016 | Jones et al. |
| 2016/0302423 A1 | 10/2016 | Jones et al. |
| 2016/0302424 A1 | 10/2016 | DiDonato et al. |
| 2016/0302425 A1 | 10/2016 | DiDonato et al. |
| 2017/0086464 A1 | 3/2017 | Floro et al. |
| 2017/0135352 A1 | 5/2017 | Breakfield et al. |
| 2017/0164618 A1 | 6/2017 | Breakfield et al. |
| 2017/0238553 A1 | 8/2017 | Jones et al. |

(Continued)

FOREIGN PATENT DOCUMENTS

| CA | 2183275 A1 | 2/1998 |
| CN | 101028008 A | 9/2007 |

(Continued)

OTHER PUBLICATIONS

"ATCC Bacteria and Bacteriophages", American Type Culture Collection, 1996, pp. 213-214, 19th Edition.

"ATCC Preservation Methods: Freezing and Freeze-Drying", 1991, pp. 5-13, 2nd Edition, ATCC.

Abanda-Nkpwatt et al., "Molecular Interaction Between Methylobacterium Extorquens and Seedlings: Growth Promotion, Methanol Consumption, and Localization of the Methanol Emission Site", Journal of Experimental Botany, Oct. 16, 2006, vol. 57 No. 15, pp. 4025-4032.

(Continued)

*Primary Examiner* — Medina A Ibrahim
(74) *Attorney, Agent, or Firm* — Stinson LLP

(57) ABSTRACT

The present invention provides both compositions comprising *Methylobacterium* and compositions comprising *Methylobacterium* that are depleted of substances that promote growth of resident microorganisms on a tomato plant or seed. Also provided are methods for improving tomato production, methods of making the compositions, and methods of treating a tomato plant, plant part, or seed with the compositions comprising *Methylobacterium*.

19 Claims, No Drawings

Specification includes a Sequence Listing.

(56) References Cited

U.S. PATENT DOCUMENTS

| | | | |
|---|---|---|---|
| 2018/0014223 | A1 | 1/2018 | Cheng et al. |
| 2018/0295841 | A1 | 10/2018 | Rioux |
| 2019/0021334 | A1 | 1/2019 | DiDonato Flora et al. |
| 2019/0116803 | A1 | 4/2019 | DiDonato Floro et al. |
| 2019/0241865 | A1 | 8/2019 | Bogosian |
| 2019/0364905 | A1 | 12/2019 | Rioux et al. |

FOREIGN PATENT DOCUMENTS

| | | | |
|---|---|---|---|
| EP | 0140723 | A1 | 5/1985 |
| EP | 2390345 | A1 | 11/2011 |
| KR | 100755509 | B1 | 9/2007 |
| KR | 20070106867 | A | 11/2007 |
| KR | 20070106868 | A | 11/2007 |
| KR | 20070111915 | A | 11/2007 |
| KR | 20080097568 | A | 11/2008 |
| KR | 100953179 | B1 | 4/2010 |
| KR | 10-1195899 | B1 | 10/2012 |
| WO | 2000/060052 | A1 | 10/2000 |
| WO | 2003046226 | A1 | 6/2003 |
| WO | 2012012671 | A2 | 1/2012 |
| WO | 2012/140212 | A2 | 10/2012 |
| WO | 2012140207 | A2 | 10/2012 |
| WO | 2013141815 | A1 | 9/2013 |
| WO | 2013181610 | A1 | 12/2013 |
| WO | 2014194189 | A1 | 12/2014 |
| WO | 2015/085063 | A1 | 6/2015 |
| WO | 2015085115 | A1 | 6/2015 |
| WO | 2015085116 | A1 | 6/2015 |
| WO | 2015085117 | A1 | 6/2015 |
| WO | 2015/142393 | A1 | 9/2015 |
| WO | 2016/069564 | A1 | 5/2016 |
| WO | 2016201284 | A2 | 12/2016 |
| WO | 2018106899 | A1 | 6/2018 |

OTHER PUBLICATIONS

Balachandar et al., "Genetic and Metabolic Diversity of Pink-Pigmented Facultative Methylotrophs in Phyllosphere of Tropical Plants", Brazilian Journal of Microbiology, 2008, pp. 68-73, vol. 39.
Chitra et al, "Multigeneric PGPR Coaggregates: A Novel Bioformulation and Delivery System for the Induction of Systemic Resistance in Rice-Xanthomonas Oryzae Pathosystem Under Lowland Condition", Golden Research Thoughts, Oct. 2013, pp. 1-10, vol. 3, No. 4.
Chitra et al.,"Multigeneric Microbial Coaggregates-Effect of Different Bioformulations of PGPR Cells on the Enhancement of PGPR Characteristics and Biocontrol Against Xanthomonas oryzae pv. oryzae in Rice Grown Under Lowland Condition", Journal of Applicable Chemistry, 2013, pp. 1132-1140, vol. 2, No. 5.
Corpe et al., "Ecology of the Methylotrophic Bacteria on Living Leaf Surfaces", FEMS Microbiology Ecology, 1989, vol. 62, pp. 243-250.
Corpe et al., "Methanol-Utilizing Bacteria Associated with Green Plants", Developments in Industrial Microbiology, 1982, pp. 483-493, vol. 23.
European Search Report for EP Application 14886191.7 dated Sep. 11, 2017.
GenBank entry FP103042, Nov. 5, 2010, retreived on Jan. 5, 2016 from http://www.ncbi.nlm.nih.gov/nuccore/254265931?sat=18&satkey-27964264.
Green, "Methylobacterium", Prokaryotes, 2006, vol. 5, Chapter 3.1.13, pp. 257-265.
Holland, "Methylobacterium and Plants", Recent Research Developments in Plant Physiology, 1997, pp. 207-213, vol. 1.
http://www.bacterio.net/methylobacterium.html, downloaded on Oct. 12, 2017, 12 pages.
International Search Report and Written Opinion dated Feb. 16, 2016, issued in PCT Patent Application No. PCT/US2015/057521.
International Search Report and Written Opinion dated Feb. 20, 2015, issued in PCT Patent Application No. PCT/US2014/068657.
International Search Report and Written Opinion dated Feb. 23, 2015, issued in PCT Patent Application No. PCT/US2014/068663.
International Search Report and Written Opinion dated Mar. 2, 2015, issued in PCT Patent Application No. PCT/US2014/068660.
International Search Report and Written Opinion dated May 1, 2016 issued in PCT Patent Application No. PCT/US2014/068611.
International Search Report and Written Opinion for PCT/US2013/043722 dated Aug. 23, 2013.
Jiang et al., "Methanotrophs: Multifunctional Bacteria with Promising Applications in Environmental Bioengineering", Biochemical Engineering Journal, May 15, 2010, pp. 277-288, vol. 49 No. 3.
Joe et al., "Development of Alginate-Based Aggregate Inoculants of *Methylobacterium* sp. and Azospirillum Brasilence Tested Under In Vitro Conditions to Promote Plant Growth", Journal of Applied Microbiology, Nov. 22, 2013, pp. 408-423, vol. 116, Issue 2.
Lidstrom et al., "Plants in the Pink: Cytokinin Production by Methylbacterium", Journal of Bacteriology, Apr. 2002, p. 1818, vol. 184, No. 7.
Madhaiyan et al., "Growth promotion and induction of systemic resistance in rice cultivar Co-47 (*Oryza sativa* L.) by *Methylobacterium* spp.", Biology and Fertility of Soils, 2005, pp. 350-358, vol. 41.
Madhaiyan et al., "Growth Promotion and Induction of Systemic Resistance in Rice Cultivar Co-47 (*Oryza sativa* L.) by *Methylobacterium* spp.", Botanical Bulletin of the Academia Sinica, 2004, pp. 315-324, vol. 45.
Madhaiyan et al., "Metal Tolerating Methylotrophic Bacteria Reduces Nickel and Cadmium Toxicity and Promotes Plant Growth of Tomato (*Lycopersicon esculentum* L.)", Chemosphere, May 23, 2007, pp. 220-228, vol. 69.
Madhaiyan et al., "Pink-Pigmented Facultative Methylotrophic Bacteria Accelerate Germination, Growth and Yield of Sugarcane Clone Co86032 (*Saccharum officinarum* L.)", Biology and Fertility of Soils, 2005, pp. 350-358, vol. 41.
NCBI, "NCBI Methylobacterium Genomes", <http://www.ncbi.nlm.nih.gov/genome>, site accessed on Sep. 27, 2018.
NCBI, "NCBI Protein WP 048446840", <https://www.ncbi.nlm.nih.gov/protein>, site accessed on Sep. 27, 2018.
Omer et al., "Plant Colonization by Pink-Pigmented Facultative Methylotrophic Bacteria (PPFMs)", FEMS Microbiology Ecology, Mar. 2004, pp. 319-326, vol. 47 No. 3.
Pacific Ag Research, "Evaluation of Efficacy Using NLS Strains as Biostimulant in Direct Seeded Cool Season Lettuce Approach", Research and Development Project Report, Winter-Summer 2015.
Poorniammal et al., "In Vitro Biocontrol Activity of Methylobacterium Extorquens Against Fungal Pathogens", International Journal of Plant Protection, 2009, pp. 59-62, vol. 2, No. 1.
Rastogi et al., "Leaf Microbiota in an Agroecosystem Spatiotemporal Variation in Bacterial Community Composition on Field-Grown Lettuce", The ISME Journal, Apr. 26, 2012. pp. 1812-1822, vol. 6.
RD4AG Lettuce Field Trial Report dated Jan. 30, 2015.
RD4AG Lettuce Field Trial Report dated May 31, 2015.
Ryu et al., "Plant Growth Substances Produced by *Methylobacterium* spp. and Their Effect on Tomato (*Lycopersicon esculentum* L.) and Red Pepper (*Capsicum annuum* L.) Growth", Journal of Microbiology and Biotechnology, 2006, pp. 1622-1628, vol. 16, No. 10.
Sundaram et al., "Bioinoculants for Sustainable and Cost Effective Production of High Quality Fibre", TMC Annual Report, TMC-MMI-2.3, 2006, pp. 1-7, Retrieved from the internet, Apr. 2, 2014, http://www.tmc.cicr.org.in/PDF/22.3.pd.
Sy, A. et al., "Methylotrophic Metabolism Is Advantageous for Methylobacterium extorquens during Colonization of Medicago truncatula under Competitive Conditions", Applied and Environmental Microbiology, 2005, pp. 7245-7252, vol. 71, No. 11.
Tani et al., "*Methlobacterium* Species Promoting Rice and Barley Growth and Interaction Specificity Revealed with Nhole-Cell Matrix-Assisted Laser Desorption/Ionization-Time-of-Flight Mass Spectrometry (MALDI-TOF/MS) Analysis" Plos One, Jun. 2015, 15 pages, vol. 10, Issue 6.
Terrasym 401 for Soybeans, NewLeaf Symbiotics, 2018, 2 pages.
Vaidehi et al., "Adhesion of Methylobacterium Cells to Rice Roots: Active Metabolism of Miropartner Determines the Degree of Adsorption Level at Rhizosphere", International Journal of Research in Pure and Applied Microbiology, 2012, pp. 54-58, vol. 2, No. 4.

(56) References Cited

OTHER PUBLICATIONS

Vuilleumier et al., "Methylobacterium Genome Sequences: A Reference Blueprint to Investigate Microbial Metabolism of C1 Compounds from Natural and Industrial Sources", Public Library of Science One, May 18, 2009, pp. 1-16; vol. 4, No. 5.
Wessman et al., "Impact of Matrix Properties on the Survival of Freeze-Dried Bacteria", Journal of the Science and Food Agriculture, 2011, pp. 2518-2528, vol. 91.
Abanda-Nkpwatt et al., "Molecular Interaction Between Methylobacterium Extorquens and Seedlings: Growth Promotion, Methanol Consumption, and Localization of the Methanol Emission Site", Journal of Experimental Botany, pp. 4025-4032, vol. 57, No. 15.
Adams, "The Principles of Freeze-Drying", Methods in Molecular Biology, 2007, pp. 15-38, vol. 368.
De Valdez et al., "Effect of Drying Medium on Residual Moisture Content and Viability of Freeze-Dried Lactic Acid Bacteria", Applied and Environmental Microbiology, Feb. 1985, pp. 413-415, vol. 49, No. 2.
Gomathy et al., "Impact of Biofertigation of Azophosmet on Cotton Yield under Dripirrigation", Research Journal of Agriculture and Biological Sciences, 2008, pp. 695-699, vol. 4, No. 6.
International Search Report and Written Opinion dated Apr. 28, 2015, issued in PCT Patent Application No. PCT/US2014/068558.
Joe et al., Development of Alginate-Based Aggregate Inoculants of *Methylobacterium* sp. and Azospirillum Brasilense Tested Under in vitro Conditions to Promote Plant Growth, Journal of Applied Microbiology, Nov. 2012, pp. 1-46.
Kongkhaem et al., "Silica-Immobilized *Methylobacterium* sp. NP3 and *Acinetobacter* sp. PK1 Degrade High Concentrations of Phenol", Letters in Applied Microbiology, May 2011, pp. 448-455, vol. 52 No. 5.
Leslie et al., "Trehalose and Sucrose Protect Both Membranes and Proteins in Intact Bacteria during Drying", Applied and Environmental Microbiology, Oct. 1995, pp. 3592-3597, vol. 61 No. 10.
Li et al., "2,4,5,-Trichlorophenol Degradation Using a Novel TiO2-Coated Biofilm Carrier: Roles of Adsorption, Photocatalysis, and Biodegradation", Environmental Science & Technology, Aug. 23, 2011, pp. 8359-8367. vol. 45. No. 19.
Ntsaluba et al., "Studies on Bioflocculant Production by *Methylobacterium* sp. Obi Isolated from a Freshwater Environment in South Africa", African Journal of Microbiology Research, Nov. 16, 2011, pp. 4533-4540, vol. 5 No. 26.
Simoes et al., "Adhesion and Biofilm Formation on Polystyrene by Drinking Water-Isolated Bacteria", Antonie van Leeuwenhoek, Apr. 20, 2010, pp. 317-329, vol. 98 No. 3.
Verhoef et al., "*Methylobacterium* sp. Isolated from a Finnish Paper Machine Produces Highly Pyruvated Galactan Exopolysaccharide", Carbohydrate Research, 2003, pp. 1851-1859, vol. 338.
Ardanov et al., "Methylobacterium-Induced Endophyte Community Changes Correspond with Protection of Plants Against Pathogen Attack", Plos One, 2012, pp. 1-8, vol. 7, No. 10.
Forry et al., "Automation of antimicrobial activity screening", AMB Express, 2016, pp. 1-10, vol. 6, No. 20.
Madhaiyan et al., "Influence of pesticides on the growth rate and plant-growth promoting traits of Gluconacetobacter diazotrophicus", Pesticide Biochemistry and Physiology, 2006, pp. 143-154, vol. 84.
Canadian Office Action and Examination Search Report for Canadian patent application No. 2,943,056, dated Dec. 4, 2020.
Ryu, et al., "Plant Growth Substances Produced by *Methylobacterium* spp. and Their Effect on Tomato (*Lycopersicon esculentum* L.) and Red Pepper (*Capsicum annuum* L.) Growth", J. Microbiol. Biotechnol., 2006, pp. 1622-1628, vol. 16, No. 10.

US 11,147,276 B2

COMPOSITIONS AND METHODS FOR IMPROVING TOMATO PRODUCTION

CROSS REFERENCE TO RELATED APPLICATIONS

This U.S. patent application is a continuation of U.S. patent application Ser. No. 15/126,483, incorporated herein by reference in its entirety, which is the 35 U.S.C. § 371 US national stage of International patent application PCT/US2014/068611, filed Dec. 4, 2014 and incorporated herein by reference in its entirety, which claims the benefit of U.S. Provisional Patent Application No. 61/954,390, filed Mar. 17, 2014, which is incorporated herein by reference in its entirety.

SEQUENCE LISTING STATEMENT

A sequence listing containing the file named 53907-138691_SL.txt which is 14,824,679 bytes (measured in MS-Windows®) and created on Dec. 3, 2014, comprises 9,188 sequences, is provided herewith via the USPTO's EFS system, and is incorporated herein by reference in its entirety.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter, Methylomonas, Methylomicrobium, Methylococcus, Methylosinus, Methylocystis, Methylosphaera, Methylocaldum*, and *Methylocella* (Lidstrom, 2006). Methanotrophs possess the enzyme methane monooxygenase, that incorporates an atom of oxygen from 02 into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum*, and *M. zatmanii*. However, *M. nidulans* is a nitrogen-fixing *Methylobacterium* that is not a PPFM (Sy et al., 2001). *Methylobacterium* are ubiquitous in nature, being found in soil, dust, fresh water, sediments, and leaf surfaces, as well as in industrial and clinical environments (Green, 2006).

SUMMARY

Provided herein are compositions comprising *Methylobacterium* that are depleted of substances that promote growth of resident bacteria on the plant or seed, compositions comprising a solid substance with adherent *Methylobacterium* grown thereon or an emulsion having *Methylobacterium* grown therein, compositions comprising certain *Methylobacterium* isolates and derivatives thereof, methods of using the compositions to improve tomato production, and methods of making the compositions. Such compositions are in certain instances referred to herein as simply "*Methylobacterium*-containing compositions". In certain embodiments, the *Methylobacterium* in the composition or that is used is strain NLS0037, a variant thereof, or a strain having polymorphic DNA markers present in NLS0037 that are absent from a strain that does not increase tomato seedling growth in comparison to an untreated control. In certain embodiments, the *Methylobacterium* in the composition or that is used is strain NLS0037 and the composition is used to treat a tomato seed. In certain embodiments, the *Methylobacterium* has at least one gene encoding at least one protein that is orthologous to a protein having an amino acid sequence of SEQ ID NO: 1-4594. In certain embodiments, the *Methylobacterium* has at least one gene encoding at least one protein that is orthologous to a protein having an amino acid sequence of SEQ ID NO: 1-4594 with the proviso that the gene is not found in *M. extorquens* AM1, *M. extorquens* PA1, or *M. extorquens* ME4. In certain embodiments, the *Methylobacterium* has at least one gene encoding a protein that is orthologous to a reference protein of Table 4. In certain embodiments, the *Methylobacterium* in the composition or that is used is a *Methylobacterium* is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* is selected from the group consisting of NLS0017 (NRRL B-50931), NLS0037 (NRRL B-50941), NLS0066 (NRRL B-50940), and derivatives thereof. In certain embodiments, any of the aforementioned compositions can further comprise an agriculturally acceptable excipient, an agriculturally acceptable adjuvant, or combination thereof.

Methods for improving tomato production comprising applying a coating or partial coating of a composition comprising *Methylobacterium* to a tomato plant, a part thereof, or to a tomato seed, wherein said composition comprises a solid substance with adherent *Methylobacterium* grown thereon, an emulsion having *Methylobacterium* grown therein, or compositions comprising certain *Methylobacterium* isolates and derivatives thereof, and wherein said tomato plant or tomato plant grown from said seed exhibits a trait improvement selected from the group consisting of an increased rate of root growth, leaf growth, seedling growth, seed production, fruit production, scion production, rootstock production, and/or increased total biomass decreased cycle time, and combinations thereof when compared to an untreated control tomato plant or a control tomato plant grown from an untreated seed are provided herein. Methods comprising applying a composition comprising *Methylobacterium* to a tomato plant, a part thereof, or to a tomato seed, wherein said composition comprises: (i) a solid substance with adherent *Methylobacterium* grown thereon; (ii) an emulsion having *Methylobacterium* grown therein; (iii) a *Methylobacterium* that has at least one gene encoding at least one protein that is orthologous to a protein having an amino acid sequence of SEQ ID NO: 1-4594; or (iv) a *Methylobacterium* selected from the group consisting of NLS0017 (NRRL B-50931), NLS0037 (NRRL B-50941), NLS0066 (NRRL B-50940), and derivatives thereof, and wherein said tomato plant or tomato plant grown from said seed exhibits a trait improvement selected from the group consisting of an increased rate of root growth, leaf growth, seedling growth, seed production, fruit production, scion production, rootstock production, and/or increased total biomass when compared to an untreated control tomato plant or a control tomato plant grown from an untreated seed, thereby obtaining improved tomato production, are also provided. In certain embodiments, the composition comprises *Methylobacterium* at a titer of about $1\times10^6$ CFU/gm to about $1\times10^{14}$ CFU/gm for a solid composition or at a titer of about $1\times10^6$ CFU/mL to about $1\times10^{11}$ CFU/mL for a liquid composition containing the solid substance or for the emulsion. In certain embodiments, the *Methylobacterium* has at least one polymorphic DNA element that is present in *Methylobacterium* strain NLS0037 but that is absent from a strain that does not increase tomato seedling growth. In certain embodiments, the applied composition coats or partially coats said plant or a part thereof, or said seed. In certain embodiments, the composition is applied in a hydroponic solution. In certain embodiments, the methods further comprise: (i) growing said tomato plant or tomato plant grown from said seed; and/or (ii) harvesting seedlings, rootstock, scions, fruit, or seed from said tomato plant or tomato plant grown from said seed. In certain embodiments, the solid substance with adherent *Methylobacterium* is not a substance that promotes growth of resident microorganisms on the tomato plant, the part thereof, or the tomato seed. In certain embodiments, the composition comprises an agriculturally acceptable adjuvant and/or excipient. In certain embodiments of any of the aforementioned methods, the composition is depleted of substances that promote growth of resident microorganisms on said plant or seed. In certain embodiments, the *Methylobacterium* has at least one gene encoding at least one protein that is orthologous to a protein having an amino acid sequence of SEQ ID NO: 1-4594. In certain embodiments, the *Methylobacterium* has at least one gene encoding at least one protein that is orthologous to a protein having an amino acid sequence of SEQ ID NO: 1-4594 with the proviso that the gene is not found in *M. extorquens* AM1, *M. extorquens* PA1, or *M. extorquens* ME4. In certain embodiments, the *Methylobacterium* has at least one gene encoding a protein that is orthologous to a reference protein of Table 4. In certain embodiments, the *Methylobacterium* is selected from the group consisting of NLS0017 (NRRL B-50931), NLS0037 (NRRL B-50941), NLS0066 (NRRL B-50940), and derivatives thereof. Also provided are tomato plant parts or tomato seeds obtained by any of the aforementioned methods and that are coated or partially coated with a composition comprising *Methylobacterium*.

Methods for improving tomato plant production comprising applying a composition comprising *Methylobacterium* to a tomato plant, a part thereof, or tomato seed, wherein said composition is depleted of substances that promote growth of resident microorganisms on said plant or seed and wherein said plant or plant grown from said seed exhibits a trait improvement selected from the group consisting of an increased rate of leaf growth, an increased rate of root growth, increased total biomass production, increased seed yield, decreased cycle time, and combinations thereof when compared to an untreated control tomato plant or a control tomato plant grown from an untreated seed. In certain embodiments, the composition comprises a solid substance with adherent *Methylobacterium* grown thereon. In certain embodiments, the solid substance is not a substance that promotes growth of resident microorganisms on the tomato plant, the part thereof, or the tomato seed. In certain embodiments, the composition comprises *Methylobacterium* at a titer of about $1\times10^6$ CFU/gm to about $1\times10^{14}$ CFU/gm. In certain embodiments, the composition comprises a liquid, a solid substance with *Methylobacterium* adhered thereto in a liquid, a solid substance with *Methylobacterium* adhered thereto in an emulsion, or an emulsion. In certain embodiments, the composition comprises *Methylobacterium* at a titer of about $1\times10^6$ CFU/mL to about $1\times10^{11}$ CFU/mL. In certain embodiments, the methods further comprise: (i) growing said tomato plant or tomato plant grown from said seed; and/or (ii) harvesting seedlings, rootstock, scions, fruit, or seed from said tomato plant or tomato plant grown from said seed. In certain embodiments, the *Methylobacterium* has at least one polymorphic DNA element that is present in at least one *Methylobacterium* strain selected from the group consisting of NLS0037 but that is absent from a strain that does not increase tomato seedling growth. In certain embodiments, the *Methylobacterium* has at least one gene encoding at least one protein that is orthologous to a protein having an amino acid sequence of SEQ ID NO: 1-4594. In certain embodiments, the *Methylobacterium* has at least one gene encoding at least one protein that is orthologous to a protein having an amino acid sequence of SEQ ID NO: 1-4594 with the proviso that the gene is not found in *M. extorquens* AM1, *M. extorquens* PA1, or *M. extorquens* ME4. In certain embodiments, the *Methylobacterium* has at least one gene encoding a protein that is orthologous to a reference protein of Table 4. In certain embodiments, the *Methylobacterium* is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* is selected from the group consisting of NLS0017 (NRRL B-50931), NLS0037 (NRRL B-50941), NLS0066 (NRRL B-50940), and derivatives thereof. In certain embodiments of any of the aforementioned methods, the composition coats or partially coats said plant or a part thereof, or said seed. In certain embodiments the tomato plant part or tomato seed is immersed or partially immersed in the composition. In certain embodiments of any of the aforementioned methods, the composition is applied in a hydroponic solution. Also provided are tomato plants, plant parts or tomato seeds obtained by any of the aforementioned methods and that are coated or partially coated with a composition comprising *Methylobacterium*.

Compositions comprising: (a) (i) a solid substance with adherent *Methylobacterium* grown thereon; (ii) an emulsion comprising *Methylobacterium*; or (iii) certain *Methylobacterium* sp. are provided. In certain embodiments, compositions comprising: (i) a solid substance with adherent *Methylobacterium* grown thereon; (ii) an emulsion with *Methylobacterium* grown therein or contained therein; or (iii) a *Methylobacterium*; wherein said *Methylobacterium* has at least one gene encoding at least one protein that is orthologous to a protein having an amino acid sequence of SEQ ID NO: 1-4594 or wherein the *Methylobacterium* has at least one gene encoding a protein that is orthologous to a reference protein of Table 4, and wherein said composition further comprises an agriculturally acceptable adjuvant and/or excipient or wherein the composition comprises a hydroponic solution of man-made origin are provided. In certain embodiments, the compositions can comprise: (i) a solid substance with adherent *Methylobacterium* grown thereon or (ii) an emulsion with *Methylobacterium* grown therein or contained therein, wherein said *Methylobacterium* has at least one gene encoding at least one protein that is orthologous to a protein having an amino acid sequence of SEQ ID NO: 1-4594 or wherein the *Methylobacterium* has at least one gene encoding a protein that is orthologous to a reference protein of Table 4, and wherein said composition further comprises an agriculturally acceptable adjuvant and/or excipient or wherein the composition comprises a hydroponic solution of man-made origin. In certain embodiments, the *Methylobacterium* has at least one gene encoding at least one protein that is orthologous to a protein having an amino acid sequence of SEQ ID NO: 1-4594 with the proviso that the gene is not found in *M. extorquens* AM1, *M. extorquens* PA1, or *M. extorquens* ME4. In certain embodiments, the *Methylobacterium* has at least one polymorphic DNA element that is present in *Methylobacterium* isolate NLS0037. In certain embodiments, the *Methylobacterium* is NLS0037 a variant thereof, or a strain having polymorphic DNA markers present in NLS0037 that are absent from a strain that does not increase tomato seedling growth in comparison to an untreated control. In certain embodiments, the *Methylobacterium* has at least one gene encoding at least one protein that is orthologous to a protein having an amino acid sequence of SEQ ID NO: 1-4594. In certain embodiments the *Methylobacterium* has at least one gene encoding a protein that is orthologous to a reference protein of Table 4. In certain embodiments, the *Methylobacterium* is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* is selected from the group consisting of NLS0017 (NRRL B-50931), NLS0037 (NRRL B-50941), NLS0066 (NRRL B-50940), and derivatives thereof. In certain embodiments, the composition is depleted of substances that promote growth of resident microorganisms on a plant or seed. In certain embodiments, the substance that promotes growth of resident microorganisms on a plant or seed is selected from the group consisting of a carbon source, a nitrogen source, a phosphorous source, a sulfur source, a magnesium source, and combinations thereof. In certain embodiments, the compositions further comprise an agriculturally acceptable adjuvant and/or excipient. In certain embodiments, the solid substance with adherent *Methylobacterium* grown thereon has a *Methylobacterium* titer of at least about $5 \times 10^8$ CFU/gm to at least about $1 \times 10^{14}$ CFU/gm. In certain embodiments, the aforementioned compositions are adapted for use in treating a tomato plant or seed or is used to treat a tomato plant or seed. Also provided herein is a tomato plant part or tomato seed that is coated or partially coated with any of the aforementioned compositions. Also provided herein is a tomato plant part or tomato seed that is immersed or partially immersed in any of the aforementioned compositions.

Also provided herein are methods of identifying compositions, plant parts, plant seeds, or processed plant products comprising *Methylobacterium* sp. NLS017 or NLS066 by assaying for the presence of nucleic acid sequences contained in SEQ ID NO: 4595-9188 in those materials. In certain embodiments, such methods can comprise subjecting a sample suspected of containing *Methylobacterium* sp. NLS017 or NLS066 to a nucleic acid analysis technique and determining that the sample contains one or more nucleic acid containing a sequence of at least about 20, 50, 100, 200, 500, or a 1000 nucleotides that is identical to at least one of SEQ ID NO: 4595-9188, wherein the presence of a sequence that is identical to at least one of SEQ ID NO: 4595-7278 is indicative of the presence of NLS017 and wherein the presence of a sequence that is identical to at least one of SEQ ID NO: 7279-9188 is indicative of the presence of NLS066. Such nucleic acid analyses include, but are not limited to, techniques based on nucleic acid hybridization, polymerase chain reactions, mass spectroscopy, nanopore based detection, branched DNA analyses, combinations thereof, and the like.

Also provided herein are methods of identifying *Methylobacterium* sp. that can confer useful traits to plants by assaying for the presence of nucleic acid sequences contained in SEQ ID NO: 4595-9188 in the *Methylobacterium* sp. In certain embodiments, such methods can comprise subjecting a candidate *Methylobacterium* sp. to a nucleic acid analysis technique and determining that the sample contains one or more nucleic acid containing a sequence of at least about 20, 50, 100, 200, 500, or a 1000 nucleotides that is identical to at least one of SEQ ID NO: 4595-9188 indicates that the candidate *Methylobacterium* sp. that can confer a useful traits to a plant. Such nucleic acid analyses include, but are not limited to, techniques based on nucleic acid hybridization, polymerase chain reactions, mass spectroscopy, nanopore based detection, branched DNA analyses, combinations thereof, and the like.

DESCRIPTION

Definitions

As used herein, the phrases "adhered thereto" and "adherent" refer to *Methylobacterium* that are associated with a solid substance by growing, or having been grown, on a solid substance.

As used herein, the phrase "agriculturally acceptable adjuvant" refers to a substance that enhances the performance of an active agent in a composition for treatment of plants and/or plant parts. In certain compositions, an active agent can comprise a mono-culture or co-culture of *Methylobacterium*.

As used herein, the phrase "agriculturally acceptable excipient" refers to an essentially inert substance that can be used as a diluent and/or carrier for an active agent in a composition for treatment of plants and/or plant parts. In certain compositions, an active agent can comprise a mono-culture or co-culture of *Methylobacterium*.

As used herein, the term "*Methylobacterium*" refers to bacteria that are facultative methylotrophs of the genus *Methylobacterium*. The term *Methylobacterium*, as used herein, thus does not encompass includes species in the genera *Methylobacter, Methylomonas, Methylomicrobium, Methylococcus, Methylosinus, Methylocystis, Methylosphaera, Methylocaldum,* and *Methylocella*, which are obligate methanotrophs.

As used herein, the phrase "co-culture of *Methylobacterium*" refers to a *Methylobacterium* culture comprising at least two strains of *Methylobacterium* or at least two species of *Methylobacterium*.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the phrase "derivatives thereof", when used in the context of a *Methylobacterium* strain, refers to any strain that is obtained from the *Methylobacterium* strain. Derivatives of a *Methylobacterium* strain include, but are not limited to, variants of the strain obtained by selection, variants of the strain selected by mutagenesis and selection, and genetically transformed isolates obtained from the *Methylobacterium* strain.

As used herein, the term "emulsion" refers to a colloidal mixture of two immiscible liquids wherein one liquid is the continuous phase and the other liquid is the dispersed phase. In certain embodiments, the continuous phase is an aqueous liquid and the dispersed phase is liquid that is not miscible, or partially miscible, in the aqueous liquid.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired *Methylobacterium* or other desired microorganisms of pre-determined identity.

As used herein, the phrase "inanimate solid substance" refers to a substance which is insoluble or partially soluble in water or aqueous solutions and which is either non-living or which is not a part of a still-living organism from which it was derived.

As used herein, the phrase "mono-culture of *Methylobacterium*" refers to a *Methylobacterium* culture consisting of a single strain of *Methylobacterium*.

As used herein, the term "peptide" refers to any polypeptide of 50 amino acid residues or less.

As used herein, the term "tomato" refers to any *Solanum lycopersicon* hybrid or variety having either a determinant or indeterminant growth habit.

As used herein, the phrase "tomato seedlings" includes tomato plants from the germination stage through all vegetative stages.

As used herein, the phrase "tomato plants" includes tomato seedlings from the germination stage through all vegetative stages and tomato plants in all reproductive stages.

As used herein, the phrase "tomato plant" is inclusive of both tomato seedlings and tomato plants in all reproductive stages.

As used herein, the term "protein" refers to any polypeptide having 51 or more amino acid residues.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of said *Methylobacterium*" refers to any pesticide that when provided in a composition comprising a fermentation product comprising a solid substance wherein a mono-culture or co-culture of *Methylobacterium* is adhered thereto, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM bacteria" refers without limitation to bacterial species in the genus *Methylobacterium* other than *M. nodulans*.

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

As used herein, the phrase "substantially all of the solid phase is suspended in the liquid phase" refers to media wherein at least 95%, 98%, or 99% of solid substance(s) comprising the solid phase are distributed throughout the liquid by agitation.

As used herein, the phrase "substantially all of the solid phase is not suspended in the liquid phase" refers to media where less than 5%, 2%, or 1% of the solid is in a particulate form that is distributed throughout the media by agitation.

As used herein, the phrase "resident microorganism" refers to resident bacteria, fungi or yeast.

As used herein, the phrase "substance that promotes growth of resident microorganisms on a plant or seed" refers to a carbon source, a nitrogen source, a phosphorous source, and combinations thereof.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

*Methylobacterium*-Containing Compositions Depleted of Substances that Promote Growth of Resident Bacteria on a Plant or Seed, Methods of their Use, and Methods of Making Compositions comprising *Methylobacterium* that are depleted of substances that promote growth of resident bacteria on a plant or seed, methods of using the compositions to improve tomato production, and methods of making the compositions are provided herein. In certain embodiments of any of the aforementioned compositions, the composition comprises a solid substance wherein a mono-culture or co-culture of *Methylobacterium* is adhered thereto. In certain embodiments where the *Methylobacterium* is adhered to a solid substance, the composition comprises a colloid formed by the solid substance wherein a mono-culture or co-culture of *Methylobacterium* is adhered thereto and a liquid. In certain embodiments, the colloid is a gel. In certain embodiments of certain aforementioned compositions, composition is an emulsion that does not contain a solid substance.

Compositions that comprise a solid substance with adherent *Methylobacterium* grown thereon is provided. In certain embodiments, the adherent *Methylobacterium* can be at a titer of at least about $5 \times 10^8$ CFU/gm to at least about $5 \times 10^{13}$ CFU/gm or about $1 \times 10^{14}$ CFU/gm and the composition is depleted of substances that promote growth of resident microorganisms on a plant or seed.

In certain embodiments, the compositions containing *Methylobacterium* provided or used herein are depleted of substances that promote growth of the resident microorganisms when one or more of those substances are absent or are essentially absent. In certain embodiments, the composition is depleted of substances that promote growth of the resident microorganisms when those substances are present at a percentage of no more than about 5%, 2%, 1%, 0.5%, 0.2%, or 0.1% of the total mass, mass/total volume, or total volume of the composition. In certain embodiments, substance that promotes growth of resident microorganisms on a plant or seed is selected from the group consisting of a carbon source, a nitrogen source, a phosphorous source, a sulfur source, a magnesium source, and combinations thereof. Carbon sources include, but are not limited to, alcohols, monosaccharides, disaccharides, polysaccharides, lipids, fatty acids, and the like. Alcohols that are depleted include, but are not limited to, methanol, ethanol, glycerol, and the like. Nitrogen sources include, but are not limited to, ammonia and various compounds containing amino groups that can be metabolized by microorganisms. In certain embodiments, the substance that is depleted is a source of two or more of a carbon source, a nitrogen source, a phosphorous source, a sulfur source, and a magnesium source. For example, the composition that is depleted of amino acids or peptides and lacks other carbon or nitrogen sources is depleted for both a carbon and a nitrogen source. In certain embodiments, the composition comprises an agriculturally acceptable adjuvant and/or excipient.

Resident microorganisms on the plant or seed include, but are not limited to bacteria, fungi, and yeast. Substances that promote the growth of such microorganisms can be identified by methods including, but not limited to, assaying the plant or seed surface for the amount or number of microorganisms present prior to exposure of the plant or seed to the substance (or to a composition containing the substance), exposing the assayed plant or seed to the substance or composition in parallel with a control composition lacking the substance, and then re-assaying the plant or seed surface for the amount or number of microorganisms present after a suitable time interval and under suitable conditions of temperature to allow growth of the resident microorganisms. Assays for numbers of microorganisms include, but are not limited to, determinations of colony forming units per an amount of plant or seed exposed to the substance and the control.

Without seeking to be limited by theory, it is believed that the compositions containing *Methylobacterium* provided or used herein that are depleted of substances that promote growth of the resident microorganisms can result in superior results in comparison to other compositions containing such substances when applied to plants, plant parts, or seeds. Such superior results are believed to include, but are not limited to, improved plant yield, pathogen resistance, insect resistance, fruit ripening and the like. While not seeking to be limited by theory, it is believed that the compositions containing *Methylobacterium* that are depleted of substances that promote growth of the resident microorganisms allow for more efficient and or extensive colonization of the plant, part thereof, or seed as competition for one or more of space or nutrients by the resident microorganisms is reduced.

Also provided herein are methods for improving tomato production that comprise applying any of the aforementioned compositions or *Methylobacterium* provided herein to a tomato plant, tomato plant part, or tomato seed, and, optionally, growing the plant and/or harvesting seedlings, rootstock, scions, fruit, or seed from the plant or a plant grown from the seed. In certain embodiments, the composition coats or partially coats the tomato plant, plant part, or seed. The treated tomato plant or plant grown from the seed exhibits an increased rate of seedling growth, increased rate of root growth, an increased rate of leaf growth, increased seed production, a decreased cycle time (from seed planting to seed, rootstock, scion, or fruit production) and/or increased total biomass compared to an untreated control tomato plant or control tomato plant grown from untreated seed, thereby obtaining improved tomato production. In certain embodiments, application of the composition provides for at least about a 5%, 10%, 15%, 20%, 30% or 40% increase in root growth rate, leaf growth rate, seed, rootstock, scion, or fruit production rate, and/or increased total biomass in the tomato plant, tomato plant part, or a tomato plant derived therefrom in comparison to an untreated control tomato plant or control tomato plant grown from an untreated seed. In certain embodiments, application of the composition provides for about a 5% or 10% to about a 15%, 20%, 25%, 30%, 35%, 40%, 45%, 50%, 60%, or 70% increase in root growth rate, leaf growth rate, seedling growth rate, seed production, fruit production, and/or increased total biomass in the plant, plant part, or a plant derived therefrom in comparison to an untreated control tomato plant or control tomato plant grown from an untreated seed. In certain embodiments, application of the composition provides for at least about a 5%, 10%, 15%, 20%, 30% or 40% decrease in cycle time (i.e. time from seed to progeny seed, to usable rootstock, to usable scion, graft, or fruit) in the treated tomato plant or a tomato plant grown from a treated seed in comparison to the untreated control tomato plant or control tomato plant grown from an untreated seed. In certain embodiments, application of the composition provides for about a 5% or 10% to about a 15%, 20%, 25%, 30%, 35%, 40%, 45%, or 50% decrease in cycle time in the treated tomato plant or a tomato plant grown from a treated seed in comparison to an untreated control tomato plant or control tomato plant grown from an untreated seed. In certain embodiments, the tomato plant part is a leaf, a stem, a flower, a root, a tuber, or a seed. In certain embodiments, the method further comprises the steps of growing the plant and/or the step of harvesting at least one plant part selected from the group consisting of a leaf, a stem, a flower, a root, a fruit, or a seed from the tomato plant or plant part. In certain embodiments of any of the aforementioned methods, the methods further comprise obtaining a processed food or feed composition from the plant or plant part. In certain embodiments, the processed food composition comprises chopped or cut tomato fruit.

Also provided are methods of making a tomato plant or tomato plant seed treatment composition that comprises *Methylobacterium* and is depleted of substances that promote growth of resident bacteria on a plant or seed is provided herein. Such method comprises (i) growing a mono-culture or co-culture of *Methylobacterium* in media that comprises an aqueous phase, a liquid phase and a solid phase, or an emulsion, thereby obtaining a *Methylobacterium*-containing media; (ii) separating the *Methylobacterium* from at least one other portion of the *Methylobacterium*-containing media; and (iii) reconstituting the *Methylobacterium* in a matrix lacking substances that promote growth of resident bacteria on a plant or seed. In certain embodiments, the separation step is effected by centrifugation, filtration, or settling of the *Methylobacterium*-containing media and removal of excess liquid or emulsion therefrom. In certain embodiments, the substance that promotes growth of resident bacteria on a plant or seed is selected from the group consisting of a carbon source, a nitrogen source, a phosphorous source, and combinations thereof. In certain embodiments, the matrix is a liquid, an emulsion, or one or more solids, and comprises an agriculturally acceptable adjuvant and/or excipient. Still in certain embodiments; the *Methylobacterium* are grown in media comprising a liquid phase and a solid substance with adherent *Methylobacterium* grown thereon. The solid substance is separated from the liquid phase of the *Methylobacterium*-containing media, and the solid substance with adherent *Methylobacterium* grown thereon is reconstituted in the aforementioned matrix. In certain embodiments of the methods, the *Methylobacterium* sp., is selected from the group consisting of *M. aminovorans, M. extorquens, M. fujisawaense, M. mesophilicum, M. radiotolerans, M. rhodesianum, M. nodulans, M. phyllosphaerae, M. thiocyanatum*, and *M. oryzae*. In certain embodiments of the methods, the *Methylobacterium* is not *M. radiotolerans* or *M. oryzae*. In certain embodiments of the methods, the *Methylobacterium* is adhered to a solid substance. In certain embodiments of the methods, the *Methylobacterium* is adhered to the solid substance is combined with a liquid to form a composition that is a colloid. In certain embodiments of the methods, the colloid is a gel. In certain embodiments of the methods, the *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion.

Methods where *Methylobacterium* are cultured in biphasic media comprising a liquid phase and a solid substance have been found to significantly increase the resultant yield of *Methylobacterium* relative to methods where the *Methylobacterium* are cultured in liquid media alone. In certain embodiments, the methods can comprise growing the *Methylobacterium* in liquid media with a particulate solid substance that can be suspended in the liquid by agitation under conditions that provide for *Methylobacterium* growth. In certain embodiments where particulate solid substances are used, at least substantially all of the solid phase can thus be suspended in the liquid phase upon agitation. Such particulate solid substances can comprise materials that are about 1 millimeter or less in length or diameter. In certain embodiments, the degree of agitation is sufficient to provide for uniform distribution of the particulate solid substance in the liquid phase and/or optimal levels of culture aeration. However, in other embodiments provided herein, at least substantially all of the solid phase is not suspended in the liquid phase, or portions of the solid phase are suspended in the liquid phase and portions of the solid phase are not suspended in the liquid phase. Non-particulate solid substances can be used in certain biphasic media where the solid phase is not suspended in the liquid phase. Such non-particulate solid substances include, but are not limited to, materials that are greater than about 1 millimeter in length or diameter. Such particulate and non-particulate solid substances also include, but are not limited to, materials that are porous, fibrous, or otherwise configured to provide for increased surface areas for adherent growth of the *Methylobacterium*. Biphasic media where portions of the solid phase are suspended in the liquid phase and portions of the solid phase are not suspended in the liquid phase can comprise a mixture of particulate and non-particulate solid substances. Such particulate and non-particulate solid substances used in any of the aforementioned biphasic media also include, but are not limited to, materials that are porous, fibrous, or otherwise configured to provide for increased surface areas for adherent growth of the *Methylobacterium*. In certain embodiments, the media comprises a colloid formed by a solid and a liquid phase. A colloid comprising a solid and a liquid can be pre-formed and added to liquid media or can be formed in media containing a solid and a liquid. Colloids comprising a solid and a liquid can be formed by subjecting certain solid substances to a chemical and/or thermal change. In certain embodiments, the colloid is a gel. In certain embodiments, the liquid phase of the media is an emulsion. In certain embodiments, the emulsion comprises an aqueous liquid and a liquid that is not miscible, or only partially miscible, in the aqueous liquid. Liquids that are not miscible, or only partially miscible, in water include, but are not limited to, any of the following: (1) liquids having a miscibility in water that is equal to or less than that of pentanol, hexanol, or heptanol at 25 degrees C.; (2) liquids comprising an alcohol, an aldehyde, a ketone, a fatty acid, a phospholipid, or any combination thereof (3) alcohols selected from the group consisting of aliphatic alcohols containing at least 5 carbons and sterols; (4) an animal oil, microbial oil, synthetic oil, plant oil, or combination thereof; and/or, (5) a plant oil is selected from the group consisting of corn, soybean, cotton, peanut, sunflower, olive, flax, coconut, palm, rapeseed, sesame seed, safflower, and combinations thereof. In certain embodiments, the immiscible or partially immiscible liquid can comprises at least about 0.02% to about 20% of the liquid phase by mass. In certain embodiments, the methods can comprise obtaining a biphasic culture media comprising the liquid, the solid, and *Methylobacterium* and incubating the culture under conditions that provide for growth of the *Methylobacterium*. Biphasic culture medias comprising the liquid, the solid, and *Methylobacterium* can be obtained by a variety of methods that include, but are not limited to, any of: (a) inoculating a biphasic media comprising the liquid and the solid substance with *Methylobacterium*; (b) inoculating the solid substance with *Methylobacterium* and then introducing the solid substance comprising the *Methylobacterium* into the liquid media; (c) inoculating the solid substance with *Methylobacterium*, incubating the *Methylobacterium* on the solid substance, and then introducing the solid substance comprising the *Methylobacterium* into the liquid media; or (d) any combination of (a), (b), or (c). Methods and compositions for growing *Methylobacterium* in biphasic media comprising a liquid and a solid are disclosed in co-assigned U.S. patent application Ser. No. 13/907,161, filed May 31, 2013, which is incorporated herein by reference in its entirety, and in co-assigned International Patent Application PCT/US13/43722, filed May 31, 2013, which is incorporated herein by reference in its entirety.

Methods where *Methylobacterium* are cultured in media comprising an emulsion have also been found to significantly increase the resultant yield of *Methylobacterium* relative to methods where the *Methylobacterium* are cultured in liquid media alone. In certain embodiments, the methods for making the compositions provided herein can comprise growing the *Methylobacterium* agent in an emulsion under conditions that provide for *Methylobacterium* growth. Medias comprising the emulsion and *Methylobacterium* can be obtained by a variety of methods that include, but are not limited to, any of: (a) inoculating a media comprising the emulsion with *Methylobacterium*; (b) inoculating the aqueous liquid with the *Methylobacterium*, introducing the non-aqueous liquid, and mixing to form an emulsion; (c) inoculating the aqueous liquid with the *Methylobacterium*, introducing the non-aqueous liquid, and mixing to form an emulsion; or (d) any combination of (a), (b), or (c). In certain embodiments, the emulsion comprises an aqueous liquid and a liquid that is not miscible, or only partially miscible, in the aqueous liquid. Non-aqueous liquids that are not miscible, or only partially miscible, in water include, but are not limited to, any of the following: (1) liquids having a miscibility in water that is equal to or less than that of n-pentanol, n-hexanol, or n-heptanol at 25 degrees C.; (2) liquids comprising an alcohol, an aldehyde, a ketone, a fatty acid, a phospholipid, or any combination thereof; (3) alcohols is selected from the group consisting of aliphatic alcohols containing at least 5, 6, or 7 carbons and sterols; (4) an animal oil, microbial oil, synthetic oil, plant oil, or combination thereof; and/or, (5) a plant oil is selected from the group consisting of corn, soybean, cotton, peanut, sunflower, olive, flax, coconut, palm, rapeseed, sesame seed, safflower, and combinations thereof. In certain embodiments, the immiscible or partially immiscible non-aqueous liquid can comprise at least about 0.02% to about 20% of the emulsion by mass. In certain embodiments, the immiscible or partially immiscible non-aqueous liquid can comprise at least about any of about 0.05%, 0.1%, 0.5%, or 1% to about 3%, 5%, 10%, or 20% of the emulsion by mass. Methods and compositions for growing *Methylobacterium* in media comprising an emulsion are disclosed in co-assigned U.S. Provisional Patent Application No. 61/829,987, filed May 31, 2013, which is incorporated herein by reference in its entirety.

In certain embodiments, the fermentation broth, fermentation broth product, or compositions that comprise *Methylobacterium* sp. can further comprise one or more introduced microorganisms of pre-determined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis, Bacillus thuringiensis, Bacillus pumilis, Pseudomonas syringae, Trichoderma harzianum, Trichoderma vixens*, and *Streptomyces lydicus* strains. Other microorganisms that are added can be genetically engineered or naturally occurring isolates that are available as pure cultures. In certain embodiments, it is anticipated that the bacterial or fungal microorganism can be provided in the fermentation broth, fermentation broth product, or composition in the form of a spore.

In certain embodiments, the liquid culture medium is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Exemplary liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria-Bertani Broth").

In general, the solid substance used in the methods and compositions that provide for the efficient growth of *Methylobacterium* can be any suitable solid substance which is insoluble or only partially soluble in water or aqueous solutions. Such suitable solid substances are also non-bacteriocidal or non-bacteriostatic with respect to *Methylobacterium* when the solid substances are provided in the liquid culture media. In certain embodiments, such suitable solid substances are also solid substances that are readily obtained in sterile form or rendered sterile. Solid substances used herein can be sterilized by any method that provides for removal of contaminating microorganisms and thus include, but are not limited to, methods such as autoclaving, irradiation, chemical treatment, and any combination thereof. These solid substances include natural substances of animal, plant, microbial, fungal, or mineral origin, manmade substances, or combinations of natural and manmade substances. In certain embodiments, the solid substances are inanimate solid substances. Inanimate solid substances of animal, plant, microbial, or fungal origin can be obtained from animals, plants, microbes, or fungi that are unviable (i.e. no longer living) or that have been rendered unviable. Diatom shells are thus inanimate solid substances when previously associated diatom algae have been removed or otherwise rendered inviable. Since diatom shells are inanimate solid substances, they are not considered to be photosynthetic organisms or photosynthetic microorganisms. In certain embodiments, solid substances include, but are not limited to, sand, silt, soil, clay, ash, charcoal, diatomaceous earth and other similar minerals, ground glass or glass beads, ground ceramic materials, ceramic beads, bentonite, kaolin, talc, perlite, mica, vermiculite, silicas, quartz powder, montmorillonite, and combinations thereof. In certain embodiments, the solid substance can be a polymer or polymeric beads. Polymers that can be used as a solid substance include, but are not limited to, various polysaccharides such as cellulosic polymers and chitinous polymers which are insoluble or only partially soluble in water or aqueous solutions, agar (i.e. galactans), and combinations thereof. In certain embodiments, the solid substance can be an insoluble or only partially soluble salt crystal. Salt crystals that can be used include, but are not limited to, insoluble or only partially soluble carbonates, chromates, sulfites, phosphates, hydroxides, oxides, and sulfides. In certain embodiments, the solid substance can be a microbial cell, fungal cell, microbial spore, or fungal spore. In certain embodiments, the solid substance can be a microbial cell or microbial spore wherein the microbial cell or microbial spore is not a photosynthetic microorganism. In certain embodiments, the microbial cell or microbial spore is not a photosynthetic microorganism, where the photosynthetic microorganism is selected from the group consisting of algae, cyanobacteria, diatoms, *Botryococcus braunii, Chlorella, Dunaliella tertiolecta, Gracilaria, Pleurochrysis carterae, Sargassum*, and *Ulva*. In still other embodiments, the solid substance can be an inactivated (i.e. unviable) microbial cell, fungal cell, microbial spore, or fungal spore. In still other embodiments, the solid substance can be a quiescent (i.e. viable but not actively dividing) microbial cell, fungal cell, microbial spore, or fungal spore. In still other embodiments, the solid substance can be cellular debris of microbial origin. In still other embodiments, the solid substance can be particulate matter from any part of a plant. Plant parts that can be used to obtain the solid substance include, but are not limited to, cobs, husks, hulls, leaves, roots, flowers, stems, barks, seeds, and combinations thereof. Products obtained from processed plant parts including, but not limited to, bagasse, wheat bran, soy grits, crushed seed cake, stover, and the like can also be used. Such plant parts, processed plants, and/or processed plant parts can be milled to obtain the solid material in a particulate form that can be used. In certain embodiments, wood or a wood product including, but not limited to, wood pulp, sawdust, shavings, and the like can be used. In certain embodiments, the solid substance can be a particulate matter from an animal(s), including, but not limited to, bone meal, gelatin, ground or powdered shells, hair, macerated hide, and the like.

In certain embodiments, the solid substance is provided in a particulate form that provides for distribution of the solid substance in the culture media. In certain embodiments, the solid substance is comprised of particle of about 2 microns to about 1000 microns in average length or average diameter. In certain embodiments, the solid substance is comprised of particle of about 1 microns to about 1000 microns in average length or average diameter. In certain embodiments, the solid substance is a particle of about 1, 2, 4, 10, 20, or 40 microns to any of about 100, 200, 500, 750, or 1000 microns in average length or average diameter. Desirable characteristics of particles used in the methods and compositions provided herein include suitable wettability such that the particles can be suspended throughout the media upon agitation.

In certain embodiments, the solid substance is provided in the media as a colloid wherein the continuous phase is a liquid and the dispersed phase is the solid. Suitable solids that can be used to form colloids in liquid media used to grow *Methylobacterium* include, but are not limited to, various solids that are referred to as hydrocolloids. Such hydrocolloids used in the media, methods and compositions provided herein can be hydrophilic polymers, of plant, animal, microbial, or synthetic origin. Hydrocolloid polymers used in the methods can contain many hydroxyl groups and/or can be polyelectrolytes. Hydrocolloid polymers used in the compositions and methods provided herein include, but are not limited to, agar, alginate, arabinoxylan, carrageenan, carboxymethylcellulose, cellulose, curdlan, gelatin, gellan, β-glucan, guar gum, gum arabic, locust bean gum, pectin, starch, xanthan gum, and mixtures thereof. In certain embodiments, the colloid used in the media, methods, and compositions provided herein can comprise a hydrocolloid polymer and one or more proteins.

In certain embodiments, the solid substance can be a solid substance that provides for adherent growth of *Methylobacterium* on the solid substance. *Methylobacterium* that are adhered to a solid substance are *Methylobacterium* that cannot be substantially removed by simply washing the solid substance with the adherent *Methylobacterium* with growth media whereas non-adherent *Methylobacterium* can be substantially removed by washing the solid substance with liquid growth media. In this context, "substantially removed" means that at least about 30%, 40%, 50%, 60%, 70%, or 80% the *Methylobacterium* present are removed when the solid substance is washed with three volumes of liquid growth media. Such washing can be effected by a variety of methods including, but not limited to, decanting liquid from a washed solid phase or passing liquid through a solid phase on a filter that permits flow through of bacteria in the liquid. In certain embodiments, the adherent *Methylobacterium* that are associated with the solid can include both *Methylobacterium* that are directly attached to the solid and/or *Methylobacterium* that are indirectly attached to the solid substance. *Methylobacterium* that are indirectly attached to the solid substance include, but are not limited to, *Methylobacterium* that are attached to another *Methylobacterium* or to another microorganism that is attached to the solid substance, *Methylobacterium* that are attached to the solid substance by being attached to another substance that is attached to the solid substance, and the like. In certain embodiments, at least 10%, 20%, 30%, 40%, 50%, 60%, 70%, 80%, 90%, 95%, 98%, 99%, 99.5% or 99.9% of the *Methylobacterium* in the fermentation broth, fermentation broth product, or compositions are *Methylobacterium* that are adhered to the solid substance. In certain embodiments, adherent *Methylobacterium* can be present on the surface of the solid substance in the fermentation broth, fermentation broth product, or composition at a density of at least about 1 *Methylobacterium*/20 square micrometers, of at least about 1 *Methylobacterium*/10 square micrometers, of at least about 1 *Methylobacterium*/10 square micrometers, of at least about 1 *Methylobacterium*/5 square micrometers, of at least about 1 *Methylobacterium*/2 square micrometers, or of at least about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/square micrometer, of at least about 1 *Methylobacterium*/10 square micrometers to about 1 *Methylobacterium*/square micrometer, of at least about 1 *Methylobacterium*/10 square micrometers to about 1 *Methylobacterium*/square micrometer, of at least about 1 *Methylobacterium*/5 square micrometers to about 1 *Methylobacterium*/square micrometer, or of at least about 1 *Methylobacterium*/2 square micrometers to about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/2 square micrometers, of at least about 1 *Methylobacterium*/10 square micrometers to about 1 *Methylobacterium*/2 square micrometers, of at least about 1 *Methylobacterium*/10 square micrometers to about 1 *Methylobacterium*/2 square micrometers, or of at least about 1 *Methylobacterium*/5 square micrometers to about 1 *Methylobacterium*/2 square micrometers. Biphasic fermentation broths provided herein can comprise a liquid phase that contains non-adherent *Methylobacterium*. In certain embodiments, titers of non-adherent *Methylobacterium* in the liquid phase can be less than about 100,000, 10,000, or 1,000 CFU/ml.

Biphasic culture methods provided can yield fermentation broths with *Methylobacterium* at a titer of greater than about $5 \times 10^8$ colony-forming units per milliliter, at a titer of greater than about $1 \times 10^9$ colony-forming units per milliliter, at a titer of greater than about $1 \times 10^{10}$ colony-forming units per milliliter, at a titer of at least about $3 \times 10^{10}$ colony-forming units per milliliter. In certain embodiments, fermentation broths provided herein can comprise *Methylobacterium* at a titer of at least about $5 \times 10^8$ colony-forming units per milliliter to at least about $3 \times 10^{10}$ colony-forming units per milliliter, at least about $5 \times 10^8$ colony-forming units per milliliter to at least about $4 \times 10^{10}$ colony-forming units per milliliter, or at least about $5 \times 10^8$ colony-forming units per milliliter to at least about $6 \times 10^{10}$ colony-forming units per milliliter. In certain embodiments, fermentation broths provided herein can comprise *Methylobacterium* at a titer of at least about $1 \times 10^9$ colony-forming units per milliliter to at least about $3 \times 10^{10}$ colony-forming units per milliliter, at least about $1 \times 10^9$ colony-forming units per milliliter to at least about $4 \times 10^{10}$ colony-forming units per milliliter, or at least about $1 \times 10^9$ colony-forming units per milliliter to at least about $6 \times 10^{10}$ colony-forming units per milliliter. In certain embodiments, fermentation broths provided herein will comprise *Methylobacterium* at a titer of at least about $1 \times 10^{10}$ colony-forming units per milliliter to at least about $3\times10^{10}$ colony-forming units per milliliter, at least about $1\times10^{10}$ colony-forming units per milliliter to at least about $4\times10^{10}$ colony-forming units per milliliter, or at least about $1\times10^{10}$ colony-forming units per milliliter to at least about $6\times10^{10}$ colony-forming units per milliliter. In certain embodiments, fermentation broths provided herein will comprise *Methylobacterium* at a titer of, at least about $3\times10^{10}$ colony-forming units per milliliter to at least about $4\times10^{10}$ colony-forming units per milliliter, or at least about $3\times10^{10}$ colony-forming units per milliliter to at least about $6\times10^{10}$ colony-forming units per milliliter.

Solid substances with adherent *Methylobacterium* can be obtained as fermentation products can be used to make various compositions useful for treating plants or plant parts to improve plant yield, plant insect resistance, plant fungal disease resistance, and/or to improve tomato production. In certain embodiments, the composition comprises *Methylobacterium* and is depleted of substances that promote growth of resident bacteria. Compositions provided herein comprising *Methylobacterium*, solid substances with *Methylobacterium* grown thereon, or comprising emulsions with *Methylobacterium* grown therein can be used to treat plants or plant parts. Plants, plant parts, and, in particular, plant seeds that have been at least partially coated or coated with the fermentation broth products or compositions comprising *Methylobacterium* are thus provided. Also provided are processed plant products that contain the fermentation broth products or compositions with *Methylobacterium* or adherent *Methylobacterium*. Solid substances with adherent *Methylobacterium* can be used to make various compositions that are particularly useful for treating plant seeds. Seeds that have been at least partially coated with the fermentation broth products or compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the solid substance used in the fermentation product or composition that at least partially coats the plant, plant part, or plant seed or that is contained in the processed plant, plant part, or seed product comprises a solid substance and associated or adherent *Methylobacterium* that can be readily identified by comparing a treated and an untreated plant, plant part, plant seed, or processed product thereof. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed.

Methods of preparing a plant or plant seed treatment composition that comprises *Methylobacterium* and is depleted of substances that promote growth of resident bacteria on a plant or seed are also provided herein. Such methods can comprise (i) growing a mono-culture or co-culture of *Methylobacterium* in media that comprises: (a) an aqueous phase; (b) a liquid phase and a solid phase; or (c) an emulsion, thereby obtaining a *Methylobacterium*-containing media; (ii) separating the *Methylobacterium* from at least one other portion of the *Methylobacterium*-containing media; and (iii) reconstituting the *Methylobacterium* in a matrix lacking substances that promote growth of resident bacteria on a plant or seed. In certain embodiments, the separation step is effected by centrifugation, filtration, or settling of the *Methylobacterium*-containing media and removal of excess liquid or emulsion therefrom. In certain embodiments where the *Methylobacterium* are grown in the presence of a solid substance, the separation will provide a fraction containing *Methylobacterium* with adherent growth to the solid substance and some non-adherent *Methylobacterium* that can be reconstituted in the matrix. In certain embodiments, the substance that promotes growth of resident bacteria on a plant or seed is selected from the group consisting of a carbon source, a nitrogen source, a phosphorous source, a sulfur source, a magnesium source, and combinations thereof. In certain embodiments, the matrix is a liquid, an emulsion, or one or more solids, and comprises an agriculturally acceptable adjuvant and/or excipient. In certain embodiments; the *Methylobacterium* are grown in media comprising a liquid phase and a solid substance with adherent *Methylobacterium* grown thereon. The solid substance is separated from the liquid phase of the *Methylobacterium*-containing media, and the solid substance with adherent *Methylobacterium* grown thereon is reconstituted in the aforementioned matrix. In certain embodiments, the matrix can be a liquid including, but not limited to, water, and aqueous buffer depleted of substances that promote growth of resident bacteria on a plant or seed, or an aqueous solution depleted of substances that promote growth of resident bacteria on a plant or seed.

In certain embodiments, the *Methylobacterium* sp. that improve tomato production can be identified by testing newly isolated candidate *Methylobacterium* sp. for the presence of polymorphic nucleic acid sequences that are present in exemplary *Methylobacterium* sp. provided herein that improve tomato seedling growth rates and that are absent from *Methylobacterium* sp. that do not improve tomato seedling growth rates. In certain embodiments, the polymorphic nucleic acid sequences that are present in the identified *Methylobacterium* sp. that improves tomato production are also present in one or more of the exemplary *Methylobacterium* sp. isolates NLS0037 provided herein that improves tomato seedling growth rate but are absent from one or more of the *Methylobacterium* sp. isolates that do not improve tomato seedling growth rates. Such nucleic acid polymorphisms that occur in the *Methylobacterium* sp. that improve tomato production can include, but are not limited to, single nucleotide polymorphisms, RFLP, AFLP and/or other DNA variations such as repetitive sequences, insertion sequences, transposons, and genomic islands occurring as a result of insertions, deletions, and substitutions (Indels) in the bacterial genome which includes both the chromosomal DNA as well as any extrachromosomal nucleic acid elements that can be present in the *Methylobacterium* sp. that improve tomato production. Such extrachromosomal nucleic acid elements include, but are not limited to, plasmids, bacteriophage DNA or RNA, and the like. Methods used to identify such nucleotide polymorphisms include, but are not limited to, single base extension (SBE) techniques, allele specific hybridization (ASH), real-time PCR detection (e.g. TaqMan™; U.S. Pat. Nos. 5,804,375; 5,538,848; 5,487,972; and 5,210,015, which are each incorporated herein by reference in their entireties), combinations of ASH and RT-PCR (KASP™ detection systems, LGC Genomics, Middlesex, UK) and deep sequencing techniques (U.S. Patent Appl. No. 20120264632, incorporated herein by reference in its entirety).

Also provided herein are compositions, methods of making the compositions, and methods of using the compositions to improve tomato production. Such improved tomato production includes, but is not limited to, increased root growth rate, leaf growth rate, seedling growth rate, seed production, fruit production, scion production, rootstock production, and/or increased total biomass in comparison to an untreated control tomato plant. In certain embodiments, the compositions or methods comprise or use any of the following *Methylobacterium* sp. isolates provided in the following Table 1 or derivatives of the isolates. In certain embodiments, such derivatives can include variants but are not limited to, variants of the isolates obtained by selection, variants of the isolates selected by mutagenesis and selection, and genetically transformed isolates obtained from the isolates.

TABLE 1

*Methylobacterium* sp. isolates

| ISOLATE No. | NLS No. | USDA ARS NRRL No.[1] |
|---|---|---|
| ISO01 | NLS0046 | NRRL B-50929 |
| ISO02 | NLS0020 | NRRL B-50930 |
| ISO03 | NLS0017 | NRRL B-50931 |
| ISO04 | NLS0042 | NRRL B-50932 |
| ISO05 | NLS0089 | NRRL B-50933 |
| ISO06 | NLS0068 | NRRL B-50934 |
| ISO07 | NLS0065 | NRRL B-50935 |
| ISO08 | NLS0069 | NRRL B-50936 |
| ISO09 | NLS0062 | NRRL B-50937 |
| ISO10 | NLS0064 | NRRL B-50938 |
| ISO11 | NLS0021 | NRRL B-50939 |
| ISO12 | NLS0066 | NRRL B-50940 |
| ISO13 | NLS0037 | NRRL B-50941 |
| ISO14 | NLS0038 | NRRL B-50942 |

[1] Deposit number for strain to be deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.

Co-assigned patent applications that disclose additional specific uses of the *Methylobacterium* strains of Table 1 such as: (1) increasing corn yield (U.S. 61/911,780, filed Dec. 4, 2013; and International Application claiming benefit of the same filed on Dec. 4, 2014); (2) increasing soybean yield (U.S. 61/911,698, filed Dec. 4, 2013; and International Application claiming benefit of the same filed on Dec. 4, 2014); (3) improving lettuce cultivation (International Patent Application PCT/US14/68558 filed on Dec. 4, 2014); (4) providing fungal disease resistance (U.S. 62/045,950, filed Sep. 4, 2014; U.S. 62/013,464, filed Jun. 17, 2014) and are each incorporated herein by reference in their entireties. Specifically incorporated herein by reference in their entireties are the genomic nucleic acid sequences of NLS017, NLS020, NLS037, NLS042, NLS065, and NLS066 that are disclosed in International Application filed on Dec. 4, 2014 and claiming benefit of U.S. 61/954,840, filed Mar. 18, 2014, and U.S. 61/911,516, filed Dec. 4, 2013. Such genomic nucleic acid sequences can be used to identify compositions, plant parts, plant seeds, or processed plant products comprising NLS017, NLS020, NLS037, NLS042, NLS065, and NLS066.

Also provided herein are *Methylobacterium* sp. that provide for improved tomato production where the *Methylobacterium* sp. have any of: (i) at least one gene encoding at least one protein that is orthologous to a protein having an amino acid sequence of SEQ ID NO: 1-4594; or (ii) at least one gene encoding at least one protein that is orthologous to a reference protein of Table 4. A *Methylobacterium* sp. has at least one gene that is orthologous to a protein having an amino acid sequence of at least one of SEQ ID NO: 1-4594, or to the corresponding SEQ ID NO of a reference protein of Table 4, when a chromosome and/or any extrachromosomal DNA in that *Methylobacterium* sp. contains a gene encoding a protein that has at least 50%, at least 60%, at least 70%, at least 80%, at least 90%, at least 95%, at least 97%, at least 98%, at least 99%, or 100% sequence identity across the entire length of the amino acid sequence of at least one of SEQ ID NO: 1-4594. The *Methylobacterium* sp. can also have at least two, three, four, six, eight, 10, 15, or 20 genes encoding proteins that are orthologous to proteins having an amino acid sequence of SEQ ID NO: 1-4594 or encoding proteins that are orthologous to the corresponding SEQ ID NO of a reference protein of Table 4. In certain embodiments, the *Methylobacterium* sp. can contain at least one gene encoding a protein that is orthologous to a reference protein having the amino acid sequence of SEQ ID NO: 1-2684 of Table 4. In certain embodiments, the *Methylobacterium* sp. can contain at least one gene encoding a protein that is orthologous to reference protein having the amino acid sequence of SEQ ID NO: 2585-4594 of Table 4. In certain embodiments, the *Methylobacterium* sp. can contain at least one gene encoding a protein that is orthologous to reference protein having the amino acid sequence of SEQ ID NO: 2969 or 212 of Table 4. Examples of proteins that are orthologous to SEQ ID NO: 2969 include, but are not limited to, the orthologous proteins identified as transcriptional regulator XRE family proteins of SEQ ID NO: 2969 and 399 that are provided in Table 4. Examples of proteins that are orthologous to SEQ ID NO: 212 include, but are not limited to, proteins having the amino acid sequence of SEQ ID NO: 212 and 2828 that are similar to proteins identified as members of the LysR family transcriptional regulators. Compositions comprising any of the aforementioned *Methylobacterium* sp. and an agriculturally acceptable excipient, adjuvant, or combination thereof are also provided along with tomato seeds or leaves that are at least partially coated with such compositions and methods of using such compositions as seed or foliar treatments to improve tomato production.

A *Methylobacterium* sp. can be determined to contain a gene encoding a protein that is orthologous to a protein having an amino acid sequence of SEQ ID NO: 1-4594 by a variety of different techniques. In certain embodiments, a *Methylobacterium* sp. can be determined to contain a gene encoding a protein that is orthologous to a protein having an amino acid sequence of SEQ ID NO: 1-4594 by assembling a complete electronic genomic sequence comprising chromosomal and extrachromosomal DNA sequences present in that *Methylobacterium* sp. with a computer and associated software, and determining if any of the open reading frames (ORF) present in that DNA sequence encode a protein having the aforementioned percent sequence identity. In such embodiments, the ORF can be identified by performing a six-way translation of the electronically assembled sequence and querying the translated with an amino acid sequence of SEQ ID NO: 1-4594 or the corresponding SEQ ID NO: of a reference protein of Table 4. In other embodiments, the present or absence of a given sequence within a *Methylobacterium* sp. an amino acid sequence of SEQ ID NO: 1-4594 or the corresponding SEQ ID NO: of a reference protein of Table 4 can be determined by a nucleic acid analysis or protein analysis technique. Examples of nucleic acid sequences that encode the proteins of SEQ ID NO:1-4594 include, but are not limited to, SEQ ID NO: 4595-9188, respectively. Such nucleic acid analyses include, but are not limited to, techniques based on nucleic acid hybridization, polymerase chain reactions, mass spectroscopy, nanopore based detection, branched DNA analyses, combinations thereof, and the like. Protein analysis techniques include, but are not limited to, immuno-detection, mass spectroscopy, combinations thereof, and the like.

Compositions provided herein that are useful for treating tomato plants or plant parts that comprise *Methylobacterium*, and/or are depleted of substances that promote growth of resident bacteria on a plant or seed, contain a solid substance with adherent *Methylobacterium* grown thereon, or that comprise emulsions with *Methylobacterium* grown therein can also further comprise an agriculturally acceptable adjuvant or an agriculturally acceptable excipient. An agriculturally acceptable adjuvant or an agriculturally acceptable excipient is typically an ingredient that does not cause undue phytotoxicity or other adverse effects when exposed to a plant or plant part. In certain embodiments, the solid substance can itself be an agriculturally acceptable adjuvant or an agriculturally acceptable excipient so long as it is not bacteriocidal or bacteriostatic to the *Methylobacterium*. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, an insecticide, a fungicide, a nematocide, and a bacteriocide. In certain embodiments, the pesticide used in the composition is a pesticide that does not substantially inhibit growth of the *Methylobacterium*. As *Methylobacterium* are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the *Methylobacterium*. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), a mixture of the composition with an emulsion, or a suspension. Any of the compositions provided herein can be used to coat or partially coat a plant, plant, part, or plant seed. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed.

Agriculturally acceptable adjuvants used in the compositions that comprise *Methylobacterium* include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants that can promote contact of the active agent with interior tissues, extenders that increase the half-life of the active agent by inhibiting environmental degradation, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/de-foaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the fermentation broths, fermentation broth products, and compositions comprising *Methylobacterium* are also provided herein. Treated plants, and treated plant parts obtained therefrom, include, but are not limited to, a tomato, plant. Plant parts that are treated include, but are not limited to, leaves, stems, flowers, roots, seeds, fruit, tubers, coleoptiles, and the like. Seeds or other propagules of any of the aforementioned plants can be treated with the fermentation broths, fermentation broth products, fermentation products, and/or compositions provided herein.

In certain embodiments, plants and/or plant parts are treated by applying the fermentation broths, fermentation broth products, fermentation products, and compositions that comprise *Methylobacterium* as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (e.g. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of a biphasic fermentation broth, a fermentation broth product, fermentation product, or compositions that comprise a solid substance with *Methylobacterium* adhered thereto are also provided herein. Also provided herein are processed plant products that comprise a solid substance with *Methylobacterium* adhered thereto. Any of the compositions provided herein can be used to coat or partially coat a plant, plant, part, or plant seed. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed.

In certain embodiments, tomato seeds are treated by exposing the seeds to the fermentation broths, fermentation broth products, fermentation products, and compositions that comprise *Methylobacterium*. Seeds can be treated with the fermentation broths, fermentation broth products, and compositions provided herein by methods including, but not limited to, imbibition, coating, spraying, and the like. In certain embodiments, surface sterilized seeds are treated with a composition comprising *Methylobacterium*. In certain embodiments, non-sterilized seeds (i.e. seeds that have not been subjected to surface sterilization) are treated with a composition comprising *Methylobacterium* that has been depleted of substances that promote growth of resident microorganisms on the seed. Seed treatments can be effected with both continuous and/or a batch seed treaters. In certain embodiments, the coated seeds may be prepared by slurrying seeds with a coating composition containing a fermentation broth, fermentation broth product, or compositions that comprise the solid substance with *Methylobacterium* and air drying the resulting product. Air drying can be accomplished at any temperature that is not deleterious to the seed or the *Methylobacterium*, but will typically not be greater than 30 degrees Centigrade. The proportion of coating that comprises a solid substance and *Methylobacterium* includes, but is not limited to, a range of 0.1 to 25% by weight of the seed, 0.5 to 5% by weight of the seed, and 0.5 to 2.5% by weight of seed. Partial coating of a seed can includes, but is not limited to coating at least about 5%, 10%, 20%, 30%, 40%, 50%, 60%, 70%, 80%, 90%, 95%, 98%, 99%, or about 99.5% of the surface area of the seed. In certain embodiments, a solid substance used in the seed coating or treatment will have *Methylobacterium* adhered thereon. In certain embodiments, a solid substance used in the seed coating or treatment will be associated with *Methylobacterium* and will be a fermentation broth, fermentation broth product, or composition obtained by the methods provided herein. Various seed treatment compositions and methods for seed treatment disclosed in U.S. Pat. Nos. 5,106,648, 5,512,069, and 8,181,388 are incorporated herein by reference in their entireties and can be adapted for use with an active agent comprising the fermentation broths, fermentation broth products, or compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, maltodextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylamide polymers and copolymers, polyhydroxyethyl acrylate, methylacrylamide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with an active agent comprising the fermentation broths, fermentation broth products, or compositions provided herein.

In certain embodiments, PPFMs that are used to increase tomato production could also be applied in a hydroponic solution as an addition to the hydroponic pool. Such hydroponic solutions are solutions comprising at least minerals necessary for tomato plant growth. Hydroponic solutions suitable for growth of tomato plants and seedlings include, but are not limited, to those described in U.S. Pat. Nos. 8,091,275 and 7,818,916, which are each incorporated herein by reference in their entireties with respect to the hydroponic solutions disclosed therein.

Provided herein are compositions that comprise *Methylobacterium* that provide increased tomato fruit, scion, or rootstock production and increased tomato seedling growth relative to untreated plants that have not been exposed to the compositions. In certain embodiments, plant parts, including, but not limited to, a seed, a leaf, a fruit, a stem, a root, a tuber, or a coleoptile can be treated with the compositions provided herein to increase tomato production. Treatments or applications can include, but are not limited to, spraying, coating, partially coating, immersing, and/or imbibing the plant or plant parts with the compositions provided herein. In certain embodiments, a seed, a leaf, a fruit, a stem, a root, a tuber, or a coleoptile can be immersed and/or imbibed with a liquid, semi-liquid, emulsion, or slurry of a composition provided herein. Such seed immersion or imbibition can be sufficient to provide for improved tomato production in a treated plant or plant part in comparison to an untreated plant or plant part. Improved tomato production includes, but is not limited, to increased seedling growth, root growth, increased leaf growth, increased seed, scion, or rootstock production, and/or increased total biomass in comparison to untreated control plants. In certain embodiments, plant seeds can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation.

Compositions provided herein comprising *Methylobacterium* are therefore expected to be useful in improving tomato production.

In certain embodiments, an amount of a composition provided herein that is sufficient to provide for improved tomato production can be a composition with *Methylobacterium* at a titer of at least about $1\times10^6$ colony-forming units per milliliter, at least about $5\times10^6$ colony-forming units per milliliter, at least about $1\times10^7$ colony-forming units per milliliter, at least about $5\times10^8$ colony-forming units per milliliter, at least about $1\times10^9$ colony-forming units per milliliter, at least about $1\times10^{10}$ colony-forming units per milliliter, or at least about $3\times10^{10}$ colony-forming units per milliliter. In certain embodiments, an amount of a composition provided herein that is sufficient to provide for improving tomato production can be a composition with *Methylobacterium* at a titer of about least about $1\times10^6$ colony-forming units per milliliter, at least about $5\times10^6$ colony-forming units per milliliter, at least about $1\times10^7$ colony-forming units per milliliter, or at least about $5\times10^8$ colony-forming units per milliliter to at least about $6\times10^{10}$ colony-forming units per milliliter of a liquid or an emulsion. In certain embodiments, an amount of a composition provided herein that is sufficient to provide for improving tomato production can be a fermentation broth product with a *Methylobacterium* titer of a solid phase of that product is at least about 5×10$^8$ colony-forming units per milliliter to at least about 5×10$^{13}$ colony-forming units of *Methylobacterium* per gram of the solid phase. In certain embodiments, an amount of a composition provided herein that is sufficient to provide for improving tomato production can be a composition with a *Methylobacterium* titer of at least about 1×10$^6$ colony-forming units per gram, at least about 5×10$^6$ colony-forming units per gram, at least about 1×10$^7$ colony-forming units per gram, or at least about 5×10$^8$ colony-forming units per gram to at least about 6×10$^{10}$ colony-forming units of *Methylobacterium* per gram of particles in the composition containing the particles that comprise a solid substance wherein a mono-culture or co-culture of *Methylobacterium* is adhered thereto. In certain embodiments, an amount of a composition provided herein that is sufficient to provide for improving tomato production can be a composition with a *Methylobacterium* titer of at least about 1×10$^6$ colony-forming units per mL, at least about 5×10$^6$ colony-forming units per mL, at least about 1×10$^7$ colony-forming units per mL, or at least about 5×10$^8$ colony-forming units per mL to at least about 6×10$^{10}$ colony-forming units of *Methylobacterium* per mL in a composition comprising an emulsion wherein a mono-culture or co-culture of a *Methylobacterium* adhered to a solid substance is provided therein or grown therein. In certain embodiments, an amount of a composition provided herein that is sufficient to provide for improving tomato production can be a composition with a *Methylobacterium* titer of at least about 1×10$^6$ colony-forming units per mL, at least about 5×10$^6$ colony-forming units per mL, at least about 1×10$^7$ colony-forming units per mL, or at least about 5×10$^8$ colony-forming units per mL to at least about 6×10$^{10}$ colony-forming units of *Methylobacterium* per mL of in a composition comprising an emulsion wherein a mono-culture or co-culture of a *Methylobacterium* is provided therein or grown therein.

In certain embodiments, an amount of a composition provided herein that is sufficient to provide for improved tomato production can be a composition with a *Methylobacterium* sp. at a titer of at least about 1×10$^4$ colony-forming units per milliliter, at least about 1×10$^5$ colony-forming units per milliliter, at least about 1×10$^6$ colony-forming units per milliliter, at least about 5×10$^6$ colony-forming units per milliliter, at least about 1×10$^7$ colony-forming units per milliliter, at least about 5×10$^8$ colony-forming units per milliliter, at least about 1×10$^9$ colony-forming units per milliliter, at least about 1×10$^{10}$ colony-forming units per milliliter, or at least about 3×10$^{10}$ colony-forming units per milliliter. In certain embodiments, an amount of a composition provided herein that is sufficient to provide for improved tomato production can be a composition with *Methylobacterium* sp. at a titer of at least about 1×10$^4$ colony-forming units per milliliter, at least about 1×10$^5$ colony-forming units per milliliter, about least about 1×10$^6$ colony-forming units per milliliter, at least about 5×10$^6$ colony-forming units per milliliter, at least about 1×10$^7$ colony-forming units per milliliter, or at least about 5×10$^8$ colony-forming units per milliliter to at least about 6×10$^{10}$ colony-forming units per milliliter of a liquid or an emulsion. In certain embodiments, an amount of a composition provided herein that is sufficient to provide for improved tomato production can be a fermentation broth product with a *Methylobacterium* sp. titer of a solid phase of that product is at least about 1×10$^4$ colony-forming units per gram, at least about 1×10$^5$ colony-forming units per gram, at least about 1×10$^6$ colony-forming units per gram, at least about 5×10$^6$ colony-forming units per gram, at least about 1×10$^7$ colony-forming units per gram, at least about 5×10$^8$ colony-forming units per gram, at least about 1×10$^9$ colony-forming units per gram, or at least about 5×10$^9$ colony-forming units per gram to at least about 6×10$^{10}$ colony-forming units of *Methylobacterium* per gram, at least about 1×10$^{11}$ colony-forming units of *Methylobacterium* per gram, at least about 1×10$^{12}$ colony-forming units of *Methylobacterium* per gram, at least about 1×10$^{13}$ colony-forming units of *Methylobacterium* per gram, or at least about 5×10$^{13}$ colony-forming units of *Methylobacterium* per gram of the solid phase. In certain embodiments, an amount of a composition provided herein that is sufficient to provide for improved tomato production can be a composition with a *Methylobacterium* titer of at least about 1×10$^6$ colony-forming units per gram, at least about 5×10$^6$ colony-forming units per gram, at least about 1×10$^7$ colony-forming units per gram, at least about 5×10$^8$ colony-forming units per gram, at least about 1×10$^9$ colony-forming units per gram, or at least about 5×10$^9$ colony-forming units per gram to at least about 6×10$^{10}$ colony-forming units of *Methylobacterium* per gram, at least about 1×10$^{11}$ colony-forming units of *Methylobacterium* per gram, at least about 1×10$^{12}$ colony-forming units of *Methylobacterium* per gram, at least about 1×10$^{13}$ colony-forming units of *Methylobacterium* per gram, or at least about 5×10$^{13}$ colony-forming units of *Methylobacterium* per gram of particles in the composition containing the particles that comprise a solid substance wherein a mono-culture or co-culture of *Methylobacterium* sp. is adhered thereto. In certain embodiments, an amount of a composition provided herein that is sufficient to provide for improved tomato production can be a composition with a *Methylobacterium* titer of at least about 1×10$^6$ colony-forming units per mL, at least about 5×10$^6$ colony-forming units per mL, at least about 1×10$^7$ colony-forming units per mL, or at least about 5×10$^8$ colony-forming units per mL to at least about 6×10$^{10}$ colony-forming units of *Methylobacterium* per mL in a composition comprising an emulsion wherein a mono-culture or co-culture of a *Methylobacterium* sp. adhered to a solid substance is provided therein or grown therein. In certain embodiments, an amount of a composition provided herein that is sufficient to provide for improved tomato production can be a composition with a *Methylobacterium* titer of at least about 1×10$^6$ colony-forming units per mL, at least about 5×10$^6$ colony-forming units per mL, at least about 1×10$^7$ colony-forming units per mL, or at least about 5×10$^8$ colony-forming units per mL to at least about 6×10$^{10}$ colony-forming units of *Methylobacterium* per mL of in a composition comprising an emulsion wherein a mono-culture or co-culture of a *Methylobacterium* sp. is provided therein or grown therein.

EXAMPLES

The following examples are included to demonstrate preferred embodiments of the invention. It will be appreciated by those of skill in the art that the techniques disclosed in the following examples represent techniques discovered by the Applicants to function well in the practice of the invention, and thus can be considered to constitute preferred modes for its practice. However, those of skill in the art should, in light of the instant disclosure, appreciate that many changes can be made in the specific embodiments that are disclosed, while still obtaining like or similar results, without departing from the scope of the invention**.

Example 1. Culturing of PPFM Strains in a Liquid Growth Media Supplemented with a Solid Substance The liquid growth medium used to culture the PPFM cultures was a base salts medium supplemented with glycerol, peptone, and diatomaceous earth. The base salts medium used was ammonium mineral salts (AMS) medium. AMS medium contains, per liter, 700 milligrams of dibasic potassium phosphate anhydrous, 540 milligrams of monobasic potassium phosphate anhydrous, one gram of magnesium sulfate heptahydrate, 500 milligrams of ammonium chloride anhydrous, and 200 milligrams of calcium chloride dihydrate.

AMS base medium was prepared from three stock solutions, listed below:

| Stock solution I: for one liter at 50X concentration | |
|---|---|
| dibasic potassium phosphate, anhydrous | 35 grams |
| monobasic potassium phosphate, anhydrous | 27 grams |
| Stock solution II: for one liter at 50X concentration | |
| magnesium sulfate heptahydrate | 50 grams |
| ammonium chloride, anhydrous | 25 grams |
| Stock solution III: for one liter at 50X concentration | |
| calcium chloride dihydrate | 10 grams |

Stock solutions I, II, and III were autoclaved separately.

To prepare one liter of liquid AMS medium with glycerol, peptone, and diatomaceous earth, the following were added to 920 ml of distilled water:
20 ml of stock solution I
20 ml of stock solution II
20 ml of stock solution III
20 ml of a 50% glycerol stock solution
10 grams of peptone
2 grams of diatomaceous earth The resulting solution with suspended diatomaceous earth was sterilized by autoclaving.

Two liters of the above AMS medium were placed into a four-liter flask. Two milliliters of liquid culture PPFMs were added to the media to inoculate. The flask was then placed in an incubated shaker set to 240 RPM and 30 degrees Celsius. The cultures were grown for six days and then stored at 4 degrees Celsius for future use.

Example 2. Seed Inoculation of Tomatoes

Commercial Sweet Olive™ tomato seeds were treated with the PPFM strain NLS0037, and then grown over a time period of about 12-14 days. The titer of strain NLS0037 was $2.0 \times 10^7$ CFU/mL. Two liters of the culture were initially grown in liquid AMS-GP media plus diatomaceous earth at 2 grams/liter (see Example 1). A 100 ml of the culture media was spun down in a centrifuge to form a pellet. The supernatant was then drained and room temperature tap water was added to bring the solution back to its initial volume of 100 ml. Seeds were planted in 100 cell Horticube sheets (an artificial growth media) and treated with 1 ml of solution applied directly to the seed by pipette at the time of planting. The growth media and watering practices simulate a hydroponic treatment. Each experimental unit (control and treated) contained 100 tomato seedlings. The wet weight of each seedling was measured, with the means being reported in Table 2.

TABLE 2

Control and PPFM Treated Tomato Seedling Wet Weights

| Strain | Control wet weight (mg) | Treated wet weight (mg) | Percentage increase | Confidence interval |
|---|---|---|---|---|
| NLS0037, test #1 | 159 | 225 | 42 | >95% |
| NLS0037, test #2 | 170 | 226 | 33 | >95% |
| NLS0037, test #3 | 156 | 194 | 24 | >95% |

Example 3. Identification of Nucleic Acid Polymorphisms Present in *Methylobacterium* that Improve Tomato Production Whole genome sequencing libraries for the Illumina™ high-throughput sequencing platform are generated for *Methylobacterium* sp. isolates provided in Table 1 using Illumina TRUSEQ™ or NEXTERA™ DNA sample preparation kits (described on the internet sites res.illumina.com/documents/products/datasheets/datasheet_truseq_dna_sampleprep_kits.pdf and res.illumina.com/documents/products/datasheets/datasheet_nextera_dna_sample_prep.pdf) using the methods described by the manufacturer. The resultant libraries are then subjected to pyrosequencing (Siqueira J F et al. J Oral Microbiol. 2012; 4: 10.3402/jom.v4i0.10743). Raw pyrosequencing-generated genomic sequence data are subjected to adaptor- and quality-based trimming for quality control. Whole-genome Shotgun Sequence Assembly (1) is achieved by assembling quality-passed data using the de novo assembler Velvet (2). For gene finding and annotation, reference training data is leveraged from TIGRFAM (9), Pfam, COG (10), and UniRef100 (11). The rRNAs are identified with RNAmmer (5), protein-coding genes are identified with Glimmer (3) or Maker (6), and tRNAs are identified with tRNAscan-SE (4). Gene functions are assigned with blastx (7), blastp (7), HMMER (8), and InterProScan against comprehensive protein databases described above (Reference Data).

Detection of polymorphisms (SNP or other DNA variations occurring as a result of insertions, deletions, and substitutions (Indels)) in the *Methylobacterium* sp. isolates of Table 1 is performed with BWA (12) and the Samtools suite (on the internet at samtools.sourceforge.net/), structural variation is identified with BreakDancer (on the internet at breakdancer.sourceforge.net/) and CoGE (on the internet at genomevolution.org/CoGe/). Polymorphisms diagnostic for *Methylobacterium* that secrete anti-fungal agents are identified by comparisons of the sequences of exemplary *Methylobacterium* isolate NLS0037 that improve tomato seedling growth but that are absent from one or more *Methylobacterium* isolates that do not improve tomato. Polymorphisms present in exemplary *Methylobacterium* isolate NLS0037 that improve tomato production but that are absent in exemplary *Methylobacterium* isolates that do not improve tomato production are then used to identify other *Methylobacterium* isolates that improve tomato production.

REFERENCES FOR EXAMPLE 4

1. Miller J R, Koren S, Sutton G (2010) Assembly algorithms for next-generation sequencing data. Genomics 95: 315-327.
2. Zerbino D R, Birney E (2008) Velvet: algorithms for de novo short read assembly using de Bruijn graphs. Genome Res 18: 821-829.

3. Delcher A L, Bratke K A, Powers E C, Salzberg S L (2007) Identifying bacterial genes and endosymbiont DNA with Glimmer. Bioinformatics 23: 673-679.
4. Lowe T M, Eddy S R (1997) tRNAscan-SE: a program for improved detection of transfer RNA genes in genomic sequence. Nucleic Acids Res 25: 955-964.
5. Lagesen K, Hallin P, Rodland E A, Staerfeldt H H, Rognes T, et al. (2007) RNAmmer: consistent and rapid annotation of ribosomal RNA genes. Nucleic Acids Res 35: 3100-3108.
6. Cantarel B, Korf I, Robb S, et al. (2008) MAKER: An easy-to-use annotation pipeline designed for emerging model organism genomes. Genome Research 18: 188-196.
7. Altschul S F, Madden T L, Schaffer A A, Zhang J, Zhang Z, et al. (1997) Gapped BLAST and PSI-BLAST: a new generation of protein database search programs. Nucleic Acids Res 25: 3389-3402.
8. Eddy S R (2009) A new generation of homology search tools based on probabilistic inference. Genome Inform 23: 205-211.
9. Haft D H, Selengut J D, White O (2003) The TIGRFAMs database of protein families. Nucleic Acids Res 31: 371-373.
10. Tatusov R L, Fedorova N D, Jackson J D, Jacobs A R, Kiryutin B, et al. (2003) The COG database: an updated version includes eukaryotes. BMC Bioinformatics 4: 41.
11. Suzek B E, Huang H, McGarvey P, Mazumder R, Wu C H (2007) UniRef: comprehensive and non-redundant UniProt reference clusters. Bioinformatics 23: 1282-1288.
12. Li H. and Durbin R. (2009) Fast and accurate short read alignment with Burrows-Wheeler Transform. Bioinformatics, 25:1754-60.

Example 5. Testing of Additional *Methylobacterium* Isolates for Stimulation of Tomato Seedling Growth

*Methylobacterium* isolates NLS0017, NLS0037, NLS0038, and NLS0066 were tested for stimulation of tomato seedling growth essentially as described in Example 2 with the exceptions that dry rather than wet weight of the seedlings was determined and that the amount applied to each seed was 0.25 mL rather than 1 mL. The results of such analyses are shown in Table 3.

TABLE 3

Percent Increase in Seedling Dry Weight relative to control for NLS0017, NLS0037, NLS0038, and NLS0066 treatments

| NLS Isolate | Percent Increase in Seedling Dry Weight relative to control | Confidence Interval |
| --- | --- | --- |
| NLS0017, | 16.4% | >95%, |
| NLS0037 | 7.4% | 93%, |
| NLS0038 | 5.6% | No statistically significant difference from control |
| NLS0066 | 23.5% | >95%, |

The NLS0017 and NLS0066 strains were identified as isolates capable of providing improved tomato seedling growth while NLS0038 was identified as an isolate that did not improve tomato seedling growth in these experiments.

Example 6. Identification of Orthologous Genes Present in *Methylobacterium* sp. that can Improve Tomato Production The PPFM strains listed in Table 1 were grown on solid agar media comprising Ammonium Mineral Salts (AMS) plus glycerol and peptone at 30° C. for 5 days, essentially as described in co-assigned U.S. Patent Application Publication No. US20130324407 and incorporated herein by reference in its entirety. Genomic DNA was extracted using MO-BIO (Carlsbad, Calif.) Ultra Clean Microbial DNA Isolation kit, and 1 μg of high quality DNA was used for Illumina Nextera XT library preparation followed by Illumina 2×100 paired-end sequencing on a HiSeq2000 system. Raw Illumina genomic sequence data were subjected to adaptor- and quality-based trimming for quality control. Whole-genome Shotgun Sequence Assembly was achieved by assembling quality-passed data using the de novo assembler SPADES (33). For gene finding and annotation, reference training data was leveraged from TIGRFAM (9), Pfam, COG (10), and UniRef100 (11). The rRNAs were identified with RNAmmer (5), protein-coding genes were identified with Glimmer (3) and Maker (6), and tRNAs were identified with tRNAscan-SE (4). Gene functions were assigned with blastx (7), blastp (7), HMMER (8), and InterProScan against comprehensive protein databases described above (Reference Data). Detection of polymorphisms (SNP or other DNA variations occurring as a result of insertions, deletions, and substitutions (Indels)) in the *Methylobacterium* sp. isolates was performed with BWA (12) and the Samtools suite (on the internet at samtools.sourceforge.net/) and the Genome Analysis Toolkit (GATK, on the world wide web internet site "broadinstitute.org/gatk/"), structural variation was identified with BreakDancer (on the internet at breakdancer.sourceforge.net/) and CoGE (on the internet at genomevolution.org/CoGe/).

Genes that encoded open reading frames were predicted from the assembled whole genomic sequences of NLS0017, NLS0038, and NLS066 essentially as described above. Within and between genome orthologous genes were clustered using OrthoMCL (available on the world wide web internet site "orthomcl.org/orthomcl/"). Putative functional annotations were assigned to gene products using BLASTP (available on the internet site "blast.ncbi.nlm.nih.gov/Blast.cgi") against the UniProt database (available on the world wide web internet site "uniprot.org/"). Genes present in individual genomes of NLS0017 and NLS0066 that could improve tomato production (as shown in Example 5) but absent in the genome of NLS0038 that did not improve tomato production (as shown in Example 5) were identified in OrthoMCL clusters using custom software. The encoded proteins found in the *Methylobacterium* NLS0017 and NLS0066 that could improve tomato production are provided in the sequencing listing as SEQ ID NO: 1-4594. The nucleic acid sequences that encode the proteins of SEQ ID NO: 1-4594 are SEQ ID NO: 4595-9188, respectively. The proteins encoded by genes present in NLS0017 but absent from NLS0038 are provided as SEQ ID NO: 1-2684. The proteins encoded by genes present in NLS0066 but absent from NLS0038 are provided as SEQ ID NO: 2685-4594. Orthologous gene groups representing genes encoding proteins found in the genomes of at least two individual genomes of NLS0017 and NLS0066 that could improve tomato production (as shown in Example 5) but that are absent in the genome of NLS0038 that did not improve tomato production are provided in Table 4. In Table 4, groups of orthologous genes are provided in each row, where the longest sequence and associated unique Seq ID Number are designated as a reference sequence to represent the ortholog cluster (Column 3 of Table 4). The ortholog group identification number is provided in column 1 of Table 4, the closest gene identity based on database comparisons is provided in column 2 of Table 4, and the reference sequence for each ortholog cluster is provided in column 3 of Table 4. Examples of ortholog sequences found in NLS0017 and NLS0066 are provided as SEQ ID NO in Table 4, columns 4, and 5, respectively.

TABLE 4

Orthologous Genes found in NLS0017 and NLS0066 that are absent in NLS0038

| Unique Ortholog Group Identifier | Annotation | Reference. Ortholog SEQ ID NO: | NLS0017 Ortholog SEQ ID NO: | NLS0066 Ortholog SEQ ID NO: |
|---|---|---|---|---|
| 1107v20141116 | membrane protein | 1 | 1 | 2685 |
| 1112v20141116 | TRAP-type transport system periplasmic component-like protein | 2 | 2 | 2686 |
| 1134v20141116 | transposase | 5 | 5 | 2687 |
| 1330v20141116 | MFS transporter | 2688 | 12 | 2688 |
| 1345v20141116 | Hypothetical protein | 14 | 14 | 2689 |
| 1770v20141116 | Crp/FNR family transcriptional regulator | 18 | 18 | 2690 |
| 3540v20141116 | hypothetical protein | 21 | 21 | 2691 |
| 3605v20141116 | porin | 22 | 22 | 2692 |
| 3664v20141116 | AraC family transcriptional regulator | 24 | 24 | 2694 |
| 3782v20141116 | hypothetical protein | 25 | 25 | 2695 |
| 3796v20141116 | Hypothetical protein | 2698 | 26 | 2698 |
| 3837v20141116 | hypothetical protein | 2700 | 28 | 2700 |
| 3924v20141116 | L-lactate dehydrogenase (cytochrome) | 30 | 30 | 2702 |
| 3930v20141116 | hypothetical protein | 2703 | 34 | 2703 |
| 3960v20141116 | sulfite:cytochrome C oxidoreductase subunit A | 2704 | 36 | 2704 |
| 3964v20141116 | transposase | 2705 | 37 | 2705 |
| 3974v20141116 | putative sulfite:cytochrome c oxidoreductase subunit B | 38 | 38 | 2706 |
| 4022v20141116 | hypothetical protein | 42 | 42 | 2707 |
| 4025v20141116 | hypothetical protein MexAM1_META1p1708 | 43 | 43 | 2708 |
| 4057v20141116 | major facilitator superfamily protein | 49 | 49 | 2709 |
| 4058v20141116 | hypothetical protein | 50 | 50 | 2710 |
| 4061v20141116 | hypothetical protein | 51 | 51 | 2711 |
| 4068v20141116 | pyruvate kinase | 52 | 52 | 2712 |
| 4075v20141116 | hypothetical protein | 2713 | 53 | 2713 |
| 4082v20141116 | FAD-dependent oxidoreductase | 55 | 55 | 2714 |
| 4084v20141116 | hypothetical protein | 2715 | 57 | 2715 |
| 4106v20141116 | ECF subfamily RNA polymerase sigma-24 factor | 2716 | 58 | 2716 |
| 4113v20141116 | short-chain dehydrogenase/reductase SDR | 59 | 59 | 2717 |
| 4124v20141116 | MarR family transcriptional regulator | 2718 | 60 | 2718 |
| 4146v20141116 | two component transcriptional regulator | 2721 | 61 | 2721 |
| 4147v20141116 | hypothetical protein | 62 | 62 | 2722 |
| 4155v20141116 | hypothetical protein Mrad2831_1363 | 64 | 64 | 2723 |
| 4162v20141116 | cobalt-containing nitrile hydratase subunit alpha | 65 | 65 | 2726 |
| 4163v20141116 | regulatory protein | 67 | 67 | 2727 |
| 4165v20141116 | formyl transferase | 2728 | 69 | 2728 |
| 4192v20141116 | aldo/keto reductase | 72 | 72 | 2729 |
| 4214v20141116 | aliphatic nitrilase | 74 | 74 | 2730 |
| 4228v20141116 | hypothetical protein | 75 | 75 | 2731 |
| 4269v20141116 | TonB-dependent siderophore receptor | 2732 | 77 | 2732 |
| 4288v20141116 | ABC transporter-like protein | 84 | 84 | 2734 |
| 4325v20141116 | FAD-dependent oxidoreductase | 91 | 91 | 2736 |
| 4327v20141116 | hypothetical protein | 92 | 92 | 2737 |
| 4335v20141116 | hypothetical protein Mrad2831_6489 | 2738 | 93 | 2738 |
| 4353v20141116 | transposase partial | 95 | 95 | 2739 |
| 4354v20141116 | magnesium transporter | 96 | 96 | 2740 |
| 4356v20141116 | spermidine/putrescine ABC transporter ATP-binding protein | 2741 | 97 | 2741 |
| 4376v20141116 | hypothetical protein | 2743 | 103 | 2743 |
| 4407v20141116 | hypothetical protein | 107 | 107 | 2744 |
| 4409v20141116 | Asp/Glu racemase | 2745 | 109 | 2745 |
| 4410v20141116 | binding-protein-dependent transport system inner membrane protein | 110 | 110 | 2746 |
| 4412v20141116 | MFS transporter | 2748 | 111 | 2748 |
| 4421v20141116 | hypothetical protein | 112 | 112 | 2751 |
| 4424v20141116 | hypothetical protein | 2752 | 113 | 2752 |
| 4442v20141116 | sulfonate ABC transporter ATP-binding lipoprotein | 117 | 117 | 2753 |
| 4460v20141116 | partition protein | 121 | 121 | 2755 |
| 4464v20141116 | extracellular ligand-binding receptor | 2756 | 123 | 2756 |
| 4466v20141116 | hypothetical protein | 2757 | 124 | 2757 |
| 4482v20141116 | hypothetical protein | 2758 | 126 | 2758 |
| 4499v20141116 | sulfolactate dehydrogenase | 127 | 127 | 2760 |
| 4505v20141116 | hypothetical protein | 2761 | 130 | 2761 |
| 4506v20141116 | ABC transporter-like protein | 131 | 131 | 2762 |
| 4507v20141116 | hypothetical protein | 2763 | 132 | 2763 |
| 4508v20141116 | inner-membrane translocator | 133 | 133 | 2764 |

TABLE 4-continued

Orthologous Genes found in NLS0017 and NLS0066 that are absent in NLS0038

| Unique Ortholog Group Identifier | Annotation | Reference. Ortholog SEQ ID NO: | NLS0017 Ortholog SEQ ID NO: | NLS0066 Ortholog SEQ ID NO: |
|---|---|---|---|---|
| 4509v20141116 | branched-chain amino acid transporter permease subunit LivH | 134 | 134 | 2765 |
| 4518v20141116 | hypothetical protein | 135 | 135 | 2766 |
| 4519v20141116 | Hypothetical protein | 2767 | 136 | 2767 |
| 4520v20141116 | MFS transporter | 137 | 137 | 2770 |
| 4522v20141116 | D-amino acid dehydrogenase small subunit | 2771 | 138 | 2771 |
| 4525v20141116 | allantoate amidohydrolase | 141 | 141 | 2772 |
| 4534v20141116 | ABC transporter ATP-binding protein | 143 | 143 | 2775 |
| 4537v20141116 | beta-lactamase | 2776 | 144 | 2776 |
| 4542v20141116 | 4-phosphopantetheinyl transferase | 2777 | 146 | 2777 |
| 4546v20141116 | hypothetical protein | 147 | 147 | 2778 |
| 4562v20141116 | hypothetical protein | 2779 | 151 | 2779 |
| 4563v20141116 | urea ABC transporter permease | 2780 | 153 | 2780 |
| 4564v20141116 | amino acid ABC transporter permease | 154 | 154 | 2782 |
| 4566v20141116 | branched-chain amino acid ABC transporter substrate-binding protein | 155 | 155 | 2784 |
| 4574v20141116 | hypothetical protein | 157 | 157 | 2787 |
| 4579v20141116 | ABC transporter substrate-binding protein | 2788 | 160 | 2788 |
| 4582v20141116 | UDP-3-0-acyl N-acetylglucosamine deacetylase | 2789 | 162 | 2789 |
| 4584v20141116 | MFS transporter | 164 | 164 | 2790 |
| 4586v20141116 | hypothetical protein | 165 | 165 | 2791 |
| 4588v20141116 | 30S ribosomal protein S13 | 2792 | 166 | 2792 |
| 4601v20141116 | nitrate ABC transporter substrate-binding protein | 2794 | 167 | 2794 |
| 4607v20141116 | glutaminase | 2795 | 170 | 2795 |
| 4610v20141116 | hypothetical protein | 171 | 171 | 2796 |
| 4612v20141116 | glyoxalase/bleomycin resistance protein/dioxygenase | 2797 | 172 | 2797 |
| 4613v20141116 | shikimate kinase | 173 | 173 | 2798 |
| 4614v20141116 | hypothetical protein | 174 | 174 | 2799 |
| 4615v20141116 | putative sulfite oxidase subunit YedY | 175 | 175 | 2800 |
| 4616v20141116 | RNA polymerase sigma factor | 176 | 176 | 2801 |
| 4619v20141116 | hypothetical protein Mrad2831_0815 | 177 | 177 | 2802 |
| 4624v20141116 | hypothetical protein Mnod_0273 | 179 | 179 | 2803 |
| 4627v20141116 | ferric reductase | 180 | 180 | 2805 |
| 4628v20141116 | hypothetical protein | 181 | 181 | 2806 |
| 4634v20141116 | hypothetical protein Mrad2831_4175 | 2807 | 185 | 2807 |
| 4642v20141116 | hypothetical protein | 187 | 187 | 2808 |
| 4644v20141116 | hypothetical protein | 2809 | 188 | 2809 |
| 4646v20141116 | hypothetical protein | 189 | 189 | 2810 |
| 4648v20141116 | hypothetical protein | 2811 | 190 | 2811 |
| 4652v20141116 | response regulator receiver protein | 192 | 192 | 2812 |
| 4654v20141116 | hypothetical protein MexAM1_META1p3794 | 193 | 193 | 2813 |
| 4656v20141116 | HupE/UreJ protein | 195 | 195 | 2814 |
| 4657v20141116 | hypothetical protein | 2815 | 196 | 2815 |
| 4659v20141116 | hypothetical protein | 198 | 198 | 2816 |
| 4661v20141116 | cupin | 2817 | 200 | 2817 |
| 4663v20141116 | hypothetical protein | 2818 | 201 | 2818 |
| 4665v20141116 | hypothetical protein | 2819 | 202 | 2819 |
| 4676v20141116 | response regulator receiver sensor hybrid histidine kinase | 204 | 204 | 2820 |
| 4681v20141116 | hypothetical protein | 205 | 205 | 2821 |
| 4683v20141116 | hypothetical protein | 2822 | 206 | 2822 |
| 4684v20141116 | hypothetical protein M446_2722 | 2823 | 207 | 2823 |
| 4686v20141116 | hypothetical protein | 208 | 208 | 2824 |
| 4687v20141116 | peptidase S14 ClpP | 209 | 209 | 2825 |
| 4688v20141116 | hypothetical protein | 210 | 210 | 2826 |
| 4689v20141116 | hypothetical protein | 2827 | 211 | 2827 |
| 4690v20141116 | LysR family transcriptional regulator | 212 | 212 | 2828 |
| 4691v20141116 | hypothetical protein | 213 | 213 | 2829 |
| 4692v20141116 | hypothetical protein | 2830 | 214 | 2830 |
| 4694v20141116 | hypothetical protein | 2831 | 215 | 2831 |
| 4695v20141116 | hypothetical protein M446_0699 | 217 | 217 | 2832 |
| 4696v20141116 | MazF family transcriptional regulator | 218 | 218 | 2833 |
| 4697v20141116 | hypothetical protein Mnod_6017 | 219 | 219 | 2834 |
| 4699v20141116 | Fmn-binding pyridoxamine 5-phosphate oxidase | 2835 | 220 | 2835 |
| 4704v20141116 | siderophore biosynthesis protein | 2836 | 222 | 2836 |
| 4705v20141116 | hypothetical protein | 2837 | 223 | 2837 |
| 4706v20141116 | sorbosone dehydrogenase | 2838 | 224 | 2838 |
| 4710v20141116 | sensor histidine kinase | 225 | 225 | 2839 |

TABLE 4-continued

Orthologous Genes found in NLS0017 and NLS0066 that are absent in NLS0038

| Unique Ortholog Group Identifier | Annotation | Reference. Ortholog SEQ ID NO: | NLS0017 Ortholog SEQ ID NO: | NLS0066 Ortholog SEQ ID NO: |
|---|---|---|---|---|
| 4715v20141116 | peptidase | 2840 | 226 | 2840 |
| 4716v20141116 | metallophosphoesterase | 227 | 227 | 2841 |
| 4720v20141116 | nitrile hydratase subunit beta | 2842 | 228 | 2842 |
| 4721v20141116 | hypothetical protein | 229 | 229 | 2843 |
| 4723v20141116 | hypothetical protein | 230 | 230 | 2844 |
| 4725v20141116 | NAD-dependent epimerase/dehydratase | 2845 | 231 | 2845 |
| 4743v20141116 | AsnC family transcriptional regulator | 233 | 233 | 2848 |
| 4750v20141116 | hypothetical protein | 2849 | 234 | 2849 |
| 4751v20141116 | hypothetical protein | 2850 | 235 | 2850 |
| 4752v20141116 | hypothetical protein | 2851 | 236 | 2851 |
| 4756v20141116 | hypothetical protein | 2852 | 237 | 2852 |
| 4757v20141116 | hypothetical protein | 2853 | 238 | 2853 |
| 4759v20141116 | peptidase M20 | 2854 | 239 | 2854 |
| 4766v20141116 | iron reductase | 2855 | 242 | 2855 |
| 4767v20141116 | hypothetical protein | 243 | 243 | 2856 |
| 4771v20141116 | AsnC family transcriptional regulator | 244 | 244 | 2857 |
| 4772v20141116 | transcriptional regulator | 245 | 245 | 2858 |
| 4774v20141116 | hypothetical protein | 2859 | 246 | 2859 |
| 4789v20141116 | fusaric acid resistance protein | 247 | 247 | 2861 |
| 4796v20141116 | pyruvate dehydrogenase | 249 | 249 | 2862 |
| 4800v20141116 | GntR family transcriptional regulator | 2863 | 250 | 2863 |
| 4801v20141116 | hypothetical protein | 251 | 251 | 2864 |
| 4802v20141116 | hypothetical protein | 252 | 252 | 2865 |
| 4806v20141116 | Protein of unknown function DUF2474 | 2866 | 255 | 2866 |
| 4811v20141116 | 2 4-dihydroxyhept-2-ene-1 7-dioic acid aldolase | 258 | 258 | 2868 |
| 4814v20141116 | hypothetical protein | 259 | 259 | 2869 |
| 4834v20141116 | DltE | 263 | 263 | 2873 |
| 4838v20141116 | methyl-accepting chemotaxis receptor/sensory transducer | 264 | 264 | 2875 |
| 4842v20141116 | hypothetical protein | 2876 | 266 | 2876 |
| 4843v20141116 | ABC transporter substrate-binding protein | 267 | 267 | 2877 |
| 4844v20141116 | ABC transporter permease | 268 | 268 | 2878 |
| 4847v20141116 | hypothetical protein | 270 | 270 | 2879 |
| 4849v20141116 | two component LuxR family transcriptional regulator | 272 | 272 | 2880 |
| 4850v20141116 | Peptidase family M20/M25/M40 protein | 273 | 273 | 2881 |
| 4851v20141116 | peptide ABC transporter permease | 2882 | 274 | 2882 |
| 4877v20141116 | DoxX family protein | 2886 | 278 | 2886 |
| 4883v20141116 | binding-protein-dependent transport system inner membrane protein | 280 | 280 | 2887 |
| 4884v20141116 | methionine ABC transporter ATP-binding protein | 281 | 281 | 2888 |
| 4885v20141116 | hypothetical protein | 282 | 282 | 2889 |
| 4907v20141116 | Glucose-methanol-choline (GMC) oxidoreductase:NAD binding site | 286 | 286 | 2892 |
| 4910v20141116 | LysR family transcriptional regulator | 289 | 289 | 2893 |
| 4911v20141116 | orotate phosphoribosyltransferase | 291 | 291 | 2894 |
| 4912v20141116 | hypothetical protein | 2895 | 292 | 2895 |
| 4917v20141116 | membrane protein | 295 | 295 | 2896 |
| 4918v20141116 | RND family efflux transporter MFP subunit | 2897 | 296 | 2897 |
| 4920v20141116 | hypothetical protein | 2899 | 298 | 2899 |
| 4921v20141116 | hypothetical protein | 299 | 299 | 2900 |
| 4923v20141116 | NLPA lipoprotein | 301 | 301 | 2901 |
| 4947v20141116 | hypothetical protein | 303 | 303 | 2906 |
| 4954v20141116 | LuxR family transcriptional regulator | 2907 | 308 | 2907 |
| 4958v20141116 | cupin | 2908 | 311 | 2908 |
| 4961v20141116 | amino acid ABC transporter | 312 | 312 | 2910 |
| 4963v20141116 | response regulator receiver protein | 314 | 314 | 2911 |
| 4983v20141116 | Hypothetical protein | 2914 | 316 | 2914 |
| 4986v20141116 | hypothetical protein | 317 | 317 | 2916 |
| 4989v20141116 | peptidase S9 | 319 | 319 | 2917 |
| 4992v20141116 | N-acetyltransferase GCN5 | 320 | 320 | 2918 |
| 4993v20141116 | glutamate carboxypeptidase | 2919 | 321 | 2919 |
| 4995v20141116 | hypothetical protein Mchl_4780 | 322 | 322 | 2920 |
| 5001v20141116 | nitrate reductase | 2921 | 325 | 2921 |
| 5016v20141116 | hypothetical protein | 327 | 327 | 2923 |
| 5017v20141116 | diguanylate cyclase | 2924 | 328 | 2924 |
| 5018v20141116 | hypothetical protein | 329 | 329 | 2925 |
| 5019v20141116 | hypothetical protein | 330 | 330 | 2926 |
| 5028v20141116 | hypothetical protein | 2928 | 335 | 2928 |
| 5030v20141116 | ABC transporter permease | 337 | 337 | 2929 |
| 5034v20141116 | carbohydrate-selective porin OprB | 339 | 339 | 2930 |

TABLE 4-continued

Orthologous Genes found in NLS0017 and NLS0066 that are absent in NLS0038

| Unique Ortholog Group Identifier | Annotation | Reference Ortholog SEQ ID NO: | NLS0017 Ortholog SEQ ID NO: | NLS0066 Ortholog SEQ ID NO: |
|---|---|---|---|---|
| 5036v20141116 | hypothetical protein | 340 | 340 | 2931 |
| 5039v20141116 | hypothetical protein | 342 | 342 | 2932 |
| 5070v20141116 | amidase | 347 | 347 | 2939 |
| 5071v20141116 | type I protein secretion ATP-binding protein HlyB | 348 | 348 | 2940 |
| 5073v20141116 | hypothetical protein | 349 | 349 | 2941 |
| 5075v20141116 | gamma carboxymuconolactone decarboxylase | 352 | 352 | 2942 |
| 5076v20141116 | D-serine dehydratase | 2943 | 353 | 2943 |
| 5085v20141116 | hypothetical protein Mchl_4781 | 2944 | 359 | 2944 |
| 5092v20141116 | ABC transporter substrate-binding protein | 365 | 365 | 2945 |
| 5099v20141116 | MarR family transcriptional regulator | 368 | 368 | 2947 |
| 5121v20141116 | histidine kinase | 371 | 371 | 2949 |
| 5124v20141116 | DSBA oxidoreductase | 373 | 373 | 2950 |
| 5125v20141116 | methyl-accepting chemotaxis sensory transducer | 2951 | 374 | 2951 |
| 5129v20141116 | crotonase | 376 | 376 | 2952 |
| 5133v20141116 | amino acid ABC transporter substrate-binding protein | 379 | 379 | 2953 |
| 5137v20141116 | ferredoxin subunit of nitrite reductase and ring-hydroxylating dioxygenase | 380 | 380 | 2954 |
| 5138v20141116 | ABC transporter | 2955 | 381 | 2955 |
| 5139v20141116 | peptide ABC transporter | 382 | 382 | 2956 |
| 5182v20141116 | hypothetical protein | 2962 | 386 | 2962 |
| 5190v20141116 | chromosome partitioning protein ParA | 391 | 391 | 2965 |
| 5196v20141116 | secretion protein HlyD family protein | 397 | 397 | 2966 |
| 5197v20141116 | hypothetical protein | 398 | 398 | 2967 |
| 5199v20141116 | XRE family transcriptional regulator | 2969 | 399 | 2969 |
| 5203v20141116 | COG0346: Lactoylglutathione lyase and related lyases | 2970 | 402 | 2970 |
| 5204v20141116 | COG3386: Gluconolactonase partial | 403 | 403 | 2971 |
| 5207v20141116 | ABC transporter permease | 2972 | 405 | 2972 |
| 5208v20141116 | ABC transporter permease | 406 | 406 | 2973 |
| 5209v20141116 | dihydroorotase | 2974 | 407 | 2974 |
| 5236v20141116 | epoxide hydrolase | 2977 | 408 | 2977 |
| 5238v20141116 | OmpA/MotB domain-containing protein | 2978 | 410 | 2978 |
| 5242v20141116 | hypothetical protein | 411 | 411 | 2979 |
| 5243v20141116 | hypothetical protein | 412 | 412 | 2980 |
| 5244v20141116 | endoribonuclease L-PSP | 413 | 413 | 2982 |
| 5245v20141116 | molybdenum cofactor biosynthesis protein | 414 | 414 | 2983 |
| 5255v20141116 | peptide ABC transporter permease | 416 | 416 | 2984 |
| 5256v20141116 | sugar ABC transporter substrate-binding protein | 417 | 417 | 2985 |
| 5257v20141116 | hypothetical protein | 2986 | 418 | 2986 |
| 5333v20141116 | xanthine dehydrogenase | 2991 | 421 | 2991 |
| 5352v20141116 | hypothetical protein | 430 | 430 | 2993 |
| 5357v20141116 | ferredoxin | 433 | 433 | 2994 |
| 5365v20141116 | 3-isopropylmalate dehydrogenase | 439 | 439 | 2995 |
| 5371v20141116 | methyl-accepting chemotaxis sensory transducer | 442 | 442 | 2996 |
| 5372v20141116 | group 1 glycosyl transferase | 2997 | 444 | 2997 |
| 5373v20141116 | chemotaxis protein CheW | 2998 | 445 | 2998 |
| 5422v20141116 | alanine racemase domain-containing protein | 451 | 451 | 3009 |
| 5423v20141116 | ArsR family transcriptional regulator | 452 | 452 | 3010 |
| 5426v20141116 | hypothetical protein | 453 | 453 | 3011 |
| 5428v20141116 | hypothetical protein | 455 | 455 | 3012 |
| 5430v20141116 | HxlR family transcriptional regulator | 3013 | 457 | 3013 |
| 5433v20141116 | peptidase C14 | 3014 | 460 | 3014 |
| 5434v20141116 | hypothetical protein | 461 | 461 | 3015 |
| 5436v20141116 | LysR family transcriptional regulator | 3016 | 463 | 3016 |
| 5442v20141116 | hypothetical protein | 3017 | 466 | 3017 |
| 5443v20141116 | hypothetical protein | 467 | 467 | 3018 |
| 5444v20141116 | hypothetical protein Mext_0240 | 468 | 468 | 3019 |
| 5445v20141116 | type 11 methyltransferase | 469 | 469 | 3020 |
| 5446v20141116 | phosphoglycerate mutase | 470 | 470 | 3021 |
| 5447v20141116 | myo-inositol-1-phosphate synthase | 3022 | 471 | 3022 |
| 5448v20141116 | chemotaxis protein CheA | 3023 | 472 | 3023 |
| 5450v20141116 | NAD-dependent epimerase/dehydratase | 3024 | 474 | 3024 |
| 5451v20141116 | radical SAM protein | 475 | 475 | 3025 |
| 5452v20141116 | Hypothetical protein | 3026 | 476 | 3026 |
| 5453v20141116 | hypothetical protein Mrad2831_1317 | 3027 | 477 | 3027 |
| 5454v20141116 | response regulator receiver modulated CheB methylesterase | 3028 | 478 | 3028 |

TABLE 4-continued

Orthologous Genes found in NLS0017 and NLS0066 that are absent in NLS0038

| Unique Ortholog Group Identifier | Annotation | Reference. Ortholog SEQ ID NO: | NLS0017 Ortholog SEQ ID NO: | NLS0066 Ortholog SEQ ID NO: |
|---|---|---|---|---|
| 5500v20141116 | porin | 484 | 484 | 3038 |
| 5506v20141116 | hypothetical protein | 3040 | 486 | 3040 |
| 5507v20141116 | hypothetical protein | 487 | 487 | 3041 |
| 5508v20141116 | hypothetical protein Mpop_0725 | 3042 | 488 | 3042 |
| 5509v20141116 | hypothetical protein | 3043 | 489 | 3043 |
| 5510v20141116 | hypothetical protein | 3044 | 490 | 3044 |
| 5516v20141116 | hypothetical protein Mpop_1265 | 491 | 491 | 3046 |
| 5517v20141116 | chromosome partitioning protein | 492 | 492 | 3047 |
| 5569v20141116 | metal dependent phosphohydrolase | 495 | 495 | 3053 |
| 5573v20141116 | hypothetical protein Mext_1867 | 497 | 497 | 3054 |
| 5580v20141116 | hypothetical protein Mpop_2258 | 3056 | 500 | 3056 |
| 5583v20141116 | hypothetical protein Mpop_3020 | 3057 | 502 | 3057 |
| 5585v20141116 | hypothetical protein Mpop_0722 | 503 | 503 | 3058 |
| 5586v20141116 | hypothetical protein Mpop_0723 | 504 | 504 | 3059 |
| 5589v20141116 | XRE family transcriptional regulator | 505 | 505 | 3060 |
| 5598v20141116 | PBS lyase | 3061 | 510 | 3061 |
| 5599v20141116 | chemotaxis protein CheY | 511 | 511 | 3062 |
| 5647v20141116 | GDP-mannose 4 6-dehydratase | 3071 | 516 | 3071 |
| 5658v20141116 | hypothetical protein Mrad2831_3432 | 517 | 517 | 3072 |
| 5662v20141116 | hypothetical protein | 520 | 520 | 3074 |
| 5665v20141116 | Hypothetical protein | 3075 | 522 | 3075 |
| 5668v20141116 | cytochrome B561 | 523 | 523 | 3076 |
| 5670v20141116 | Phosphoribosylaminoimidazole-succinocarboxamide synthase | 3077 | 525 | 3077 |
| 5673v20141116 | chemotaxis sensory transducer protein | 527 | 527 | 3078 |
| 5778v20141116 | hypothetical protein | 3089 | 548 | 3089 |
| 5784v20141116 | hypothetical protein | 3090 | 552 | 3090 |
| 5785v20141116 | hypothetical protein | 3091 | 554 | 3091 |
| 5786v20141116 | Sulfur oxidation protein SoxZ | 557 | 557 | 3092 |
| 5787v20141116 | sulfur oxidation cytochrome c protein SoxA | 558 | 558 | 3093 |
| 5788v20141116 | MFS transporter | 560 | 560 | 3094 |
| 5789v20141116 | mandelate racemase/muconate lactonizing protein | 3095 | 561 | 3095 |
| 5792v20141116 | PAS domain-containing protein | 563 | 563 | 3096 |
| 5793v20141116 | sugar transporter | 3097 | 564 | 3097 |
| 5843v20141116 | Hypothetical protein | 569 | 569 | 3106 |
| 5849v20141116 | hypothetical protein Mrad2831_5253 | 3107 | 575 | 3107 |
| 5851v20141116 | chemotaxis protein | 576 | 576 | 3108 |
| 5852v20141116 | AsnC family transcriptional regulator | 3109 | 577 | 3109 |
| 5854v20141116 | hypothetical protein | 3110 | 578 | 3110 |
| 5855v20141116 | hypothetical protein | 3111 | 579 | 3111 |
| 5856v20141116 | NAD-glutamate dehydrogenase | 3112 | 580 | 3112 |
| 5857v20141116 | hypothetical protein | 581 | 581 | 3113 |
| 5860v20141116 | transcriptional regulator XRE family | 3114 | 584 | 3114 |
| 5862v20141116 | 2-nitropropane dioxygenase | 3116 | 585 | 3116 |
| 5926v20141116 | dioxygenase | 3126 | 588 | 3126 |
| 5929v20141116 | gamma-glutamyltransferase | 589 | 589 | 3128 |
| 5930v20141116 | RND efflux system outer membrane lipoprotein NodT family | 3129 | 590 | 3129 |
| 5936v20141116 | Hypothetical protein | 592 | 592 | 3130 |
| 5938v20141116 | Cytochrome c class I | 593 | 593 | 3131 |
| 5939v20141116 | hypothetical protein | 3132 | 594 | 3132 |
| 5988v20141116 | extracellular ligand-binding receptor | 600 | 600 | 3144 |
| 5993v20141116 | hypothetical protein Mrad2831_6386 | 604 | 604 | 3145 |
| 6001v20141116 | transporter | 606 | 606 | 3147 |
| 6006v20141116 | Leu/Ile/Val-binding family protein | 3148 | 608 | 3148 |
| 6007v20141116 | hypothetical protein | 609 | 609 | 3149 |
| 6010v20141116 | hypothetical protein Mrad2831_1535 | 610 | 610 | 3150 |
| 6012v20141116 | hypothetical protein | 3151 | 613 | 3151 |
| 6014v20141116 | hypothetical protein | 614 | 614 | 3152 |
| 6016v20141116 | family 5 extracellular solute-binding protein | 616 | 616 | 3153 |
| 6017v20141116 | acyl-CoA dehydrogenase | 3154 | 617 | 3154 |
| 6021v20141116 | diguanylate cyclase | 618 | 618 | 3157 |
| 6023v20141116 | hydroxymethylglutaryl-CoA lyase | 3158 | 619 | 3158 |
| 6024v20141116 | hypothetical protein | 3159 | 620 | 3159 |
| 6026v20141116 | NAD-binding 3-hydroxyacyl-CoA dehydrogenase | 3160 | 621 | 3160 |
| 6027v20141116 | L-carnitine dehydratase/bile acid-inducible protein F | 622 | 622 | 3161 |
| 6093v20141116 | Fe—S type tartrate/fumarate subfamily hydro-lyase subunit alpha | 625 | 625 | 3166 |
| 6095v20141116 | hypothetical protein | 3167 | 626 | 3167 |
| 6101v20141116 | glutathione S-transferase | 627 | 627 | 3168 |

TABLE 4-continued

Orthologous Genes found in NLS0017 and NLS0066 that are absent in NLS0038

| Unique Ortholog Group Identifier | Annotation | Reference. Ortholog SEQ ID NO: | NLS0017 Ortholog SEQ ID NO: | NLS0066 Ortholog SEQ ID NO: |
|---|---|---|---|---|
| 6115v20141116 | NAD-dependent epimerase/dehydratase | 629 | 629 | 3171 |
| 6116v20141116 | sorbosone dehydrogenase | 630 | 630 | 3172 |
| 6117v20141116 | cytochrome C | 3173 | 631 | 3173 |
| 6118v20141116 | hypothetical protein Mrad2831_0725 | 632 | 632 | 3174 |
| 6119v20141116 | serine/threonine protein phosphatase | 3175 | 633 | 3175 |
| 6124v20141116 | hypothetical protein | 636 | 636 | 3176 |
| 6125v20141116 | malate synthase G | 3177 | 637 | 3177 |
| 6126v20141116 | LysR family transcriptional regulator | 3178 | 638 | 3178 |
| 6130v20141116 | alanine racemase | 641 | 641 | 3179 |
| 6131v20141116 | 3-hydroxyisobutyrate dehydrogenase | 3180 | 642 | 3180 |
| 6133v20141116 | acyl carrier protein | 644 | 644 | 3181 |
| 6134v20141116 | hypothetical protein | 645 | 645 | 3182 |
| 6135v20141116 | hypothetical protein | 3183 | 646 | 3183 |
| 6137v20141116 | hypothetical protein | 3184 | 648 | 3184 |
| 6142v20141116 | L-carnitine dehydratase/bile acid-inducible protein F | 649 | 649 | 3185 |
| 6143v20141116 | acetolactate synthase | 3186 | 650 | 3186 |
| 6188v20141116 | GntR family transcriptional regulator | 656 | 656 | 3194 |
| 6193v20141116 | hypothetical protein | 657 | 657 | 3195 |
| 6194v20141116 | FAD linked oxidase domain-containing protein | 658 | 658 | 3196 |
| 6200v20141116 | TRAP transporter solute receptor TAXI family protein | 3197 | 662 | 3197 |
| 6201v20141116 | hypothetical protein Mext_2439 | 3198 | 663 | 3198 |
| 6202v20141116 | alpha/beta hydrolase | 664 | 664 | 3199 |
| 6203v20141116 | electron transporter | 3200 | 665 | 3200 |
| 6204v20141116 | hypothetical protein | 666 | 666 | 3201 |
| 6205v20141116 | hypothetical protein | 667 | 667 | 3202 |
| 6206v20141116 | amine oxidase | 3203 | 668 | 3203 |
| 6207v20141116 | 2-hydroxyacid dehydrogenase | 669 | 669 | 3204 |
| 6209v20141116 | hypothetical protein | 3205 | 670 | 3205 |
| 6210v20141116 | Bcr/CflA subfamily drug resistance transporter | 3206 | 671 | 3206 |
| 6214v20141116 | acyl-CoA dehydrogenase domain-containing protein | 3207 | 672 | 3207 |
| 6219v20141116 | acyl-CoA dehydrogenase | 674 | 674 | 3208 |
| 6220v20141116 | succinate-semialdehyde dehydrogenase | 675 | 675 | 3209 |
| 6221v20141116 | dihydrodipicolinate synthetase | 676 | 676 | 3210 |
| 6225v20141116 | hypothetical protein | 680 | 680 | 3211 |
| 6226v20141116 | potassium-transporting ATPase subunit B | 3212 | 681 | 3212 |
| 6229v20141116 | type III effector Hrp-dependent protein | 3213 | 682 | 3213 |
| 6230v20141116 | LacI family transcriptional regulator | 3214 | 683 | 3214 |
| 6231v20141116 | putative aldolase | 684 | 684 | 3215 |
| 6233v20141116 | glycosyl transferase family 1 | 685 | 685 | 3216 |
| 6235v20141116 | hypothetical protein | 687 | 687 | 3217 |
| 6236v20141116 | serine/threonine dehydratase | 688 | 688 | 3218 |
| 6238v20141116 | hypothetical protein | 689 | 689 | 3219 |
| 6239v20141116 | oxidase | 690 | 690 | 3220 |
| 6241v20141116 | SPW repeat-containing protein | 3221 | 693 | 3221 |
| 6243v20141116 | tartronate semialdehyde reductase | 694 | 694 | 3222 |
| 6245v20141116 | ABC transporter permease | 695 | 695 | 3223 |
| 6246v20141116 | binding-protein-dependent transport system inner membrane protein | 3224 | 696 | 3224 |
| 6247v20141116 | ABC transporter substrate-binding protein | 3225 | 697 | 3225 |
| 6248v20141116 | spermidine/putrescine ABC transporter ATPase | 698 | 698 | 3226 |
| 6249v20141116 | dihydropyrimidinase | 699 | 699 | 3227 |
| 6250v20141116 | poly-beta-hydroxybutyrate polymerase | 700 | 700 | 3228 |
| 6253v20141116 | aldo/keto reductase | 3229 | 702 | 3229 |
| 6254v20141116 | circadian phase modifier CpmA | 703 | 703 | 3230 |
| 6325v20141116 | hypothetical protein | 709 | 709 | 3231 |
| 6328v20141116 | GCN5 family acetyltransferase | 712 | 712 | 3232 |
| 6329v20141116 | MFS transporter | 713 | 713 | 3233 |
| 6331v20141116 | major facilitator superfamily protein | 715 | 715 | 3234 |
| 6332v20141116 | L-carnitine dehydratase/bile acid-inducible protein F | 3235 | 716 | 3235 |
| 6333v20141116 | hypothetical protein | 3236 | 717 | 3236 |
| 6334v20141116 | dihydroxy-acid dehydratase | 3237 | 718 | 3237 |
| 6337v20141116 | 3-hydroxyisobutyrate dehydrogenase | 3238 | 721 | 3238 |
| 6340v20141116 | 2-dehydropantoate 2-reductase | 724 | 724 | 3239 |
| 6343v20141116 | cytochrome C | 726 | 726 | 3240 |
| 6346v20141116 | hypothetical protein | 3241 | 729 | 3241 |
| 6347v20141116 | alanine racemase | 730 | 730 | 3242 |

TABLE 4-continued

Orthologous Genes found in NLS0017 and NLS0066 that are absent in NLS0038

| Unique Ortholog Group Identifier | Annotation | Reference Ortholog SEQ ID NO: | NLS0017 Ortholog SEQ ID NO: | NLS0066 Ortholog SEQ ID NO: |
|---|---|---|---|---|
| 6348v20141116 | hypothetical protein | 3243 | 731 | 3243 |
| 6351v20141116 | D-galactarate dehydratase | 733 | 733 | 3244 |
| 6353v20141116 | LysR family transcriptional regulator | 734 | 734 | 3245 |
| 6358v20141116 | 3-hydroxy-2-methylbutyryl-CoA dehydrogenase | 3246 | 735 | 3246 |
| 6413v20141116 | flagellar protein FlgA | 736 | 736 | 3254 |
| 6414v20141116 | altronate dehydratase | 737 | 737 | 3255 |
| 6415v20141116 | D-isomer specific 2-hydroxyacid dehydrogenase NAD-binding subunit | 738 | 738 | 3256 |
| 6423v20141116 | flp fap pilin component | 739 | 739 | 3257 |
| 6430v20141116 | inner-membrane translocator | 744 | 744 | 3258 |
| 6431v20141116 | sn-glycerol-3-phosphate ABC transporter substrate-binding protein | 745 | 745 | 3259 |
| 6432v20141116 | hypothetical protein | 746 | 746 | 3260 |
| 6435v20141116 | family 5 extracellular solute-binding protein | 3261 | 748 | 3261 |
| 6438v20141116 | hypothetical protein | 3262 | 749 | 3262 |
| 6440v20141116 | gamma-glutamyltransferase | 751 | 751 | 3263 |
| 6441v20141116 | prolyl-tRNA synthetase | 752 | 752 | 3264 |
| 6444v20141116 | HAD-superfamily phosphatase subfamily IIIC domain protein | 3265 | 753 | 3265 |
| 6445v20141116 | 4-methylmuconolactone transporter | 3266 | 754 | 3266 |
| 6446v20141116 | GCN5 family acetyltransferase | 755 | 755 | 3267 |
| 6449v20141116 | hypothetical protein | 757 | 757 | 3268 |
| 6452v20141116 | diguanylate cyclase/phosphodiesterase | 759 | 759 | 3269 |
| 6453v20141116 | putative alkaline phosphatase | 760 | 760 | 3270 |
| 6454v20141116 | binding-protein-dependent transport system inner membrane protein | 761 | 761 | 3271 |
| 6456v20141116 | hypothetical protein | 3272 | 763 | 3272 |
| 6457v20141116 | amidase | 3273 | 764 | 3273 |
| 6460v20141116 | iron-containing alcohol dehydrogenase | 3274 | 765 | 3274 |
| 6461v20141116 | acetyl-CoA acetyltransferase | 766 | 766 | 3275 |
| 6462v20141116 | pimeloyl-CoA dehydrogenase large subunit | 767 | 767 | 3276 |
| 6463v20141116 | acyl-CoA dehydrogenase | 768 | 768 | 3277 |
| 6465v20141116 | IclR family transcriptional regulator | 769 | 769 | 3278 |
| 6466v20141116 | hypothetical protein Mnod_2193 | 770 | 770 | 3279 |
| 6469v20141116 | acetylornithine deacetylase | 3280 | 772 | 3280 |
| 6578v20141116 | hypothetical protein | 775 | 775 | 3289 |
| 6580v20141116 | ABC transporter substrate-binding protein | 776 | 776 | 3290 |
| 6581v20141116 | hypothetical protein | 777 | 777 | 3291 |
| 6586v20141116 | dimethylmenaquinone methyltransferase | 3292 | 779 | 3292 |
| 6589v20141116 | hypothetical protein | 3293 | 781 | 3293 |
| 6594v20141116 | GntR family transcriptional regulator | 3295 | 785 | 3295 |
| 6595v20141116 | LysR family transcriptional regulator | 786 | 786 | 3296 |
| 6600v20141116 | methylase | 789 | 789 | 3297 |
| 6605v20141116 | 4-phytase | 792 | 792 | 3298 |
| 6609v20141116 | amino acid ABC transporter substrate-binding protein | 3299 | 796 | 3299 |
| 6610v20141116 | ABC transporter permease | 797 | 797 | 3300 |
| 6611v20141116 | hypothetical protein | 798 | 798 | 3301 |
| 6673v20141116 | peptide ABC transporter substrate-binding protein | 800 | 800 | 3316 |
| 6674v20141116 | ABC transporter ATP-binding protein | 3317 | 801 | 3317 |
| 6679v20141116 | MucR family transcriptional regulator | 802 | 802 | 3318 |
| 6681v20141116 | XRE family transcriptional regulator | 804 | 804 | 3319 |
| 6682v20141116 | hypothetical protein | 805 | 805 | 3320 |
| 6685v20141116 | hypothetical protein | 808 | 808 | 3321 |
| 6688v20141116 | hypothetical protein | 3322 | 811 | 3322 |
| 6689v20141116 | catalase | 3323 | 812 | 3323 |
| 6690v20141116 | hypothetical protein | 3324 | 813 | 3324 |
| 6699v20141116 | hypothetical protein Mrad2831_3163 | 3325 | 822 | 3325 |
| 6700v20141116 | hypothetical protein | 823 | 823 | 3326 |
| 6702v20141116 | hypothetical protein | 825 | 825 | 3327 |
| 6703v20141116 | fatty acid metabolism AMP-binding protein | 3328 | 826 | 3328 |
| 6704v20141116 | hypothetical protein | 3329 | 827 | 3329 |
| 6706v20141116 | DeoR family transcriptional regulator | 829 | 829 | 3330 |
| 6707v20141116 | glucarate dehydratase | 3331 | 830 | 3331 |
| 6708v20141116 | PAS/PAC sensor protein | 831 | 831 | 3332 |
| 6709v20141116 | hypothetical protein | 832 | 832 | 3333 |
| 6710v20141116 | hypothetical protein | 3334 | 833 | 3334 |
| 6711v20141116 | hypothetical protein | 3335 | 834 | 3335 |
| 6712v20141116 | hypothetical protein Mrad2831_5112 | 835 | 835 | 3336 |
| 6714v20141116 | alcohol dehydrogenase | 836 | 836 | 3338 |
| 6715v20141116 | hypothetical protein | 3339 | 837 | 3339 |

TABLE 4-continued

Orthologous Genes found in NLS0017 and NLS0066 that are absent in NLS0038

| Unique Ortholog Group Identifier | Annotation | Reference. Ortholog SEQ ID NO: | NLS0017 Ortholog SEQ ID NO: | NLS0066 Ortholog SEQ ID NO: |
|---|---|---|---|---|
| 6716v20141116 | hypothetical protein | 838 | 838 | 3340 |
| 6718v20141116 | hypothetical protein | 3341 | 840 | 3341 |
| 6719v20141116 | hypothetical protein | 841 | 841 | 3342 |
| 6721v20141116 | hypothetical protein Mrad2831_3655 | 3343 | 843 | 3343 |
| 6722v20141116 | hypothetical protein Mrad2831_0445 | 844 | 844 | 3344 |
| 6724v20141116 | hypothetical protein | 3345 | 845 | 3345 |
| 6729v20141116 | hypothetical protein | 850 | 850 | 3346 |
| 6731v20141116 | photo system reaction center subunit H | 3347 | 853 | 3347 |
| 6732v20141116 | hypothetical protein Mrad2831_3817 | 854 | 854 | 3348 |
| 6736v20141116 | hypothetical protein Mrad2831_2399 | 856 | 856 | 3349 |
| 6737v20141116 | hypothetical protein | 3350 | 857 | 3350 |
| 6738v20141116 | hypothetical protein | 3351 | 858 | 3351 |
| 6742v20141116 | epimerase | 3352 | 861 | 3352 |
| 6743v20141116 | hypothetical protein | 3353 | 862 | 3353 |
| 6800v20141116 | NAD-binding D-isomer specific 2-hydroxyacid dehydrogenase | 3363 | 867 | 3363 |
| 6806v20141116 | ArsR family transcriptional regulator | 3364 | 872 | 3364 |
| 6807v20141116 | cysteine dioxygenase | 3365 | 873 | 3365 |
| 6808v20141116 | hypothetical protein | 874 | 874 | 3366 |
| 6809v20141116 | (2Fe—2S)-binding domain-containing protein | 875 | 875 | 3367 |
| 6810v20141116 | aldehyde dehydrogenase | 876 | 876 | 3368 |
| 6811v20141116 | hypothetical protein Mnod_6032 | 3369 | 877 | 3369 |
| 6812v20141116 | histone deacetylase | 878 | 878 | 3370 |
| 6818v20141116 | hypothetical protein | 882 | 882 | 3371 |
| 6896v20141116 | hypothetical protein Mrad2831_5186 | 3379 | 894 | 3379 |
| 6903v20141116 | diguanylate cyclase | 897 | 897 | 3380 |
| 6907v20141116 | translation initiation factor IF-2 | 3381 | 899 | 3381 |
| 6909v20141116 | hypothetical protein | 3382 | 902 | 3382 |
| 6921v20141116 | acetyl-CoA carboxylase | 913 | 913 | 3383 |
| 6927v20141116 | binding-protein-dependent transport system inner membrane protein | 917 | 917 | 3384 |
| 6936v20141116 | hypothetical protein | 924 | 924 | 3385 |
| 6938v20141116 | hypothetical protein | 926 | 926 | 3386 |
| 6940v20141116 | domain of unknown function family protein | 3387 | 928 | 3387 |
| 6943v20141116 | transposase IS4 family protein | 930 | 930 | 3388 |
| 7006v20141116 | binding-protein-dependent transport system inner membrane protein | 3396 | 932 | 3396 |
| 7015v20141116 | hypothetical protein | 940 | 940 | 3397 |
| 7017v20141116 | hypothetical protein | 942 | 942 | 3398 |
| 7023v20141116 | type III restriction endonuclease subunit R | 3399 | 947 | 3399 |
| 7027v20141116 | LysR family transcriptional regulator | 3400 | 950 | 3400 |
| 7029v20141116 | hypothetical protein | 951 | 951 | 3402 |
| 7040v20141116 | hypothetical protein | 963 | 963 | 3403 |
| 7042v20141116 | arginine ABC transporter ATP-binding protein | 965 | 965 | 3404 |
| 7048v20141116 | glyoxalase | 969 | 969 | 3405 |
| 7050v20141116 | urea ABC transporter ATP-binding protein UrtD | 3406 | 971 | 3406 |
| 7051v20141116 | urea ABC transporter ATP-binding protein UrtE | 972 | 972 | 3407 |
| 7053v20141116 | hypothetical protein | 973 | 973 | 3408 |
| 7054v20141116 | GntR family transcriptional regulator | 3409 | 974 | 3409 |
| 7127v20141116 | hypothetical protein Mnod_6985 | 3416 | 983 | 3416 |
| 7152v20141116 | hydratase/decarboxylase | 3418 | 1001 | 3418 |
| 7153v20141116 | putative membrane protein | 1002 | 1002 | 3419 |
| 7155v20141116 | Lipopolysaccharide biosynthesis protein-like protein | 3420 | 1004 | 3420 |
| 7156v20141116 | aldolase | 1005 | 1005 | 3421 |
| 7163v20141116 | glycerophosphoryl diester phosphodiesterase | 1011 | 1011 | 3422 |
| 7180v20141116 | adenylate cyclase | 1027 | 1027 | 3423 |
| 7189v20141116 | hypothetical protein VOLCADRAFT_119358 | 1034 | 1034 | 3425 |
| 7190v20141116 | Glyoxalase/Bleomycin resistance protein/Dioxygenase superfamily | 3426 | 1035 | 3426 |
| 7200v20141116 | competence protein ComEA | 1046 | 1046 | 3427 |
| 7201v20141116 | serine/threonine dehydratase | 1047 | 1047 | 3428 |
| 7202v20141116 | serine--glyoxylate aminotransferase | 1048 | 1048 | 3429 |
| 7211v20141116 | cytochrome C oxidase subunit III | 1057 | 1057 | 3430 |
| 7290v20141116 | succinate dehydrogenase and fumarate reductase iron-sulfur protein | 3435 | 1064 | 3435 |
| 7291v20141116 | succinate dehydrogenase membrane anchor | 1065 | 1065 | 3436 |
| 7292v20141116 | succinate dehydrogenase cytochrome b subunit | 1066 | 1066 | 3437 |

TABLE 4-continued

Orthologous Genes found in NLS0017 and NLS0066 that are absent in NLS0038

| Unique Ortholog Group Identifier | Annotation | Reference. Ortholog SEQ ID NO: | NLS0017 Ortholog SEQ ID NO: | NLS0066 Ortholog SEQ ID NO: |
|---|---|---|---|---|
| 7293v20141116 | L(+)-tartrate or fumarate dehydratase subunit beta | 1067 | 1067 | 3438 |
| 7294v20141116 | fumarate reductase | 1068 | 1068 | 3439 |
| 7295v20141116 | YCII-like protein | 1069 | 1069 | 3440 |
| 7299v20141116 | glycosyltransferase family 2 | 3441 | 1071 | 3441 |
| 7310v20141116 | ABC transporter substrate-binding protein | 3442 | 1074 | 3442 |
| 7311v20141116 | glutathione ABC transporter permease GsiD | 1075 | 1075 | 3443 |
| 7312v20141116 | oligopeptide/dipeptide ABC transporter ATPase | 1076 | 1076 | 3444 |
| 7313v20141116 | ABC transporter-like protein | 1077 | 1077 | 3445 |
| 7314v20141116 | sodium:calcium antiporter | 3446 | 1078 | 3446 |
| 7315v20141116 | methionyl-tRNA formyltransferase | 1079 | 1079 | 3447 |
| 7317v20141116 | hypothetical protein | 1080 | 1080 | 3449 |
| 7326v20141116 | glycosyl transferase family protein | 1088 | 1088 | 3450 |
| 7331v20141116 | hypothetical protein Mrad2831_4126 | 3452 | 1090 | 3452 |
| 7332v20141116 | 4-oxalomesaconate hydratase | 1091 | 1091 | 3453 |
| 7340v20141116 | hypothetical protein FAES_2018 | 1098 | 1098 | 3454 |
| 7341v20141116 | hypothetical protein M446_1279 | 3455 | 1099 | 3455 |
| 7343v20141116 | hypothetical protein | 3456 | 1101 | 3456 |
| 7349v20141116 | diguanylate cyclase | 3457 | 1107 | 3457 |
| 7350v20141116 | hypothetical protein | 1108 | 1108 | 3458 |
| 7354v20141116 | acetyl-CoA synthetase | 1111 | 1111 | 3459 |
| 7355v20141116 | phenylacetic acid degradation protein | 1112 | 1112 | 3460 |
| 7356v20141116 | alcohol dehydrogenase | 3461 | 1113 | 3461 |
| 7357v20141116 | nitrate/sulfonate/bicarbonate ABC transporter periplasmic ligand-binding protein | 3462 | 1114 | 3462 |
| 7358v20141116 | nitrate ABC transporter permease | 3463 | 1115 | 3463 |
| 7360v20141116 | hypothetical protein | 1117 | 1117 | 3464 |
| 7363v20141116 | hypothetical protein Mrad2831_1876 | 1120 | 1120 | 3465 |
| 7365v20141116 | hypothetical protein Mrad2831_6026 | 3467 | 1121 | 3467 |
| 7368v20141116 | enoyl-CoA hydratase/isomerase | 3468 | 1124 | 3468 |
| 7370v20141116 | nitrate ABC transporter ATPase | 1126 | 1126 | 3469 |
| 7372v20141116 | hypothetical protein | 3470 | 1128 | 3470 |
| 7472v20141116 | hypothetical protein Mext_2440 | 1131 | 1131 | 3482 |
| 7478v20141116 | porin | 3483 | 1132 | 3483 |
| 7485v20141116 | branched-chain amino acid ABC transporter permease | 1138 | 1138 | 3484 |
| 7538v20141116 | RND family efflux transporter MFP subunit | 3488 | 1185 | 3488 |
| 7554v20141116 | phosphoheptose isomerase | 3490 | 1198 | 3490 |
| 7555v20141116 | GHMP kinase | 3491 | 1199 | 3491 |
| 7570v20141116 | IclR family transcriptional regulator | 1215 | 1215 | 3492 |
| 7695v20141116 | extracellular ligand-binding receptor | 1233 | 1233 | 3506 |
| 7707v20141116 | metal-dependent phosphohydrolase | 1243 | 1243 | 3508 |
| 7711v20141116 | 2-hydroxyacid dehydrogenase | 3509 | 1247 | 3509 |
| 7729v20141116 | amino acid ABC transporter | 3510 | 1264 | 3510 |
| 7730v20141116 | GntR family transcriptional regulator | 1265 | 1265 | 3511 |
| 7750v20141116 | alpha-amylase | 1283 | 1283 | 3512 |
| 7856v20141116 | hypothetical protein | 3528 | 1303 | 3528 |
| 7868v20141116 | hypothetical protein | 1313 | 1313 | 3529 |
| 7877v20141116 | hypothetical protein Mchl_0532 | 3530 | 1319 | 3530 |
| 7879v20141116 | glycosyl transferase | 3531 | 1321 | 3531 |
| 7885v20141116 | binding-protein-dependent transport system inner membrane protein | 1327 | 1327 | 3532 |
| 7888v20141116 | hypothetical protein Mrad2831_1281 | 3533 | 1330 | 3533 |
| 7890v20141116 | taurine ABC transporter permease | 1332 | 1332 | 3534 |
| 7913v20141116 | D-lactate dehydrogenase | 1351 | 1351 | 3536 |
| 8053v20141116 | acetyltransferase | 1371 | 1371 | 3558 |
| 8080v20141116 | hypothetical protein | 1397 | 1397 | 3560 |
| 8092v20141116 | ABC transporter inner membrane protein | 3561 | 1406 | 3561 |
| 8093v20141116 | ABC transporter | 1407 | 1407 | 3562 |
| 8094v20141116 | nitrate/sulfonate/bicarbonate ABC transporter | 3563 | 1408 | 3563 |
| 8109v20141116 | Hypothetical protein | 1423 | 1423 | 3564 |
| 8113v20141116 | adenylate/guanylate cyclase | 3565 | 1427 | 3565 |
| 8114v20141116 | polysaccharide deacetylase | 1428 | 1428 | 3566 |
| 8300v20141116 | Holliday junction DNA helicase RuvB | 1471 | 1471 | 3588 |
| 8301v20141116 | None | 3589 | 1472 | 3589 |
| 8310v20141116 | monooxygenase | 1480 | 1480 | 3590 |
| 8313v20141116 | GDP-L-fucose synthase | 1483 | 1483 | 3591 |
| 8314v20141116 | NAD-dependent epimerase/dehydratase | 1484 | 1484 | 3592 |
| 8315v20141116 | NAD-dependent epimerase/dehydratase | 1485 | 1485 | 3593 |
| 8318v20141116 | hypothetical protein | 1488 | 1488 | 3594 |

TABLE 4-continued

Orthologous Genes found in NLS0017 and NLS0066 that are absent in NLS0038

| Unique Ortholog Group Identifier | Annotation | Reference. Ortholog SEQ ID NO: | NLS0017 Ortholog SEQ ID NO: | NLS0066 Ortholog SEQ ID NO: |
|---|---|---|---|---|
| 8331v20141116 | hypothetical protein | 1498 | 1498 | 3595 |
| 8335v20141116 | hypothetical protein | 3596 | 1502 | 3596 |
| 8473v20141116 | ABC transporter-like protein | 1521 | 1521 | 3616 |
| 8485v20141116 | hypothetical protein | 1532 | 1532 | 3618 |
| 8524v20141116 | oxidoreductase | 1570 | 1570 | 3619 |
| 8573v20141116 | alkanal monooxygenase | 1614 | 1614 | 3620 |
| 8579v20141116 | hypothetical protein | 1620 | 1620 | 3621 |
| 8922v20141116 | response regulator receiver protein | 3641 | 1749 | 3641 |
| 9277v20141116 | transposase | 1821 | 1821 | 3684 |
| 9290v20141116 | diguanylate cyclase | 1834 | 1834 | 3685 |
| 9309v20141116 | XRE family transcriptional regulator | 3687 | 1847 | 3687 |
| 9777v20141116 | hypothetical protein | 1934 | 1934 | 3729 |
| 10194v20141116 | RTX toxins and related Ca2+-binding protein | 1954 | 1954 | 3783 |
| 10335v20141116 | hypothetical protein Mnod_7733 | 2033 | 2033 | 3794 |
| 10354v20141116 | Hypothetical protein | 3795 | 2048 | 3795 |
| 10358v20141116 | hypothetical protein | 2050 | 2050 | 3797 |
| 12071v20141116 | None | 2288 | 2288 | 4101 |
| 12161v20141116 | hypothetical protein MexAM1_META1p3214 | 4103 | 2360 | 4103 |
| 14172v20141116 | Fis family transcriptional regulator | 2469 | 2469 | 4343 |

REFERENCES FOR EXAMPLE 6

1. Miller J R, Koren S, Sutton G (2010) Assembly algorithms for next-generation sequencing data. Genomics 95: 315-327.
2. Zerbino D R, Birney E (2008) Velvet: algorithms for de novo short read assembly using de Bruijn graphs. Genome Res 18: 821-829.
3. Delcher A L, Bratke K A, Powers E C, Salzberg S L (2007) Identifying bacterial genes and endosymbiont DNA with Glimmer. Bioinformatics 23: 673-679.
4. Lowe T M, Eddy S R (1997) tRNAscan-S E: a program for improved detection of transfer RNA genes in genomic sequence. Nucleic Acids Res 25: 955-964.
5. Lagesen K, Hallin P, Rodland E A, Staerfeldt H H, Rognes T, et al. (2007) RNAmmer: consistent and rapid annotation of ribosomal RNA genes. Nucleic Acids Res 35: 3100-3108.
6. Cantarel B, Korf I, Robb S, et al. (2008) MAKER: An easy-to-use annotation pipeline designed for emerging model organism genomes. Genome Research 18: 188-196.
7. Altschul S F, Madden T L, Schaffer A A, Zhang J, Zhang Z, et al. (1997) Gapped BLAST and PSI-BLAST: a new generation of protein database search programs. Nucleic Acids Res 25: 3389-3402.
8. Eddy S R (2009) A new generation of homology search tools based on probabilistic inference. Genome Inform 23: 205-211.
9. Haft D H, Selengut J D, White O (2003) The TIGRFAMs database of protein families. Nucleic Acids Res 31: 371-373.
10. Tatusov R L, Fedorova N D, Jackson J D, Jacobs A R, Kiryutin B, et al. (2003) The COG database: an updated version includes eukaryotes. BMC Bioinformatics 4: 41.
11. Suzek B E, Huang H, McGarvey P, Mazumder R, Wu C H (2007) UniRef: comprehensive and non-redundant UniProt reference clusters. Bioinformatics 23: 1282-1288.
12. Li H. and Durbin R. (2009) Fast and accurate short read alignment with Burrows-Wheeler Transform. Bioinformatics, 25:1754-60

Other References

1. Abanda-Nkpwatt, D., M. Musch, J. Tschiersch, M. Boettner, and W. Schwab. 2006. Molecular interaction between *Methylobacterium extorquens* and seedlings: growth promotion, methanol consumption, and localization of the methanol emission site. J. Exp. Bot. 57: 4025-4032.
2. Broekaert W F, Terras F R, Cammue B P, Vanderleyden J (1990) An automated quantitative assay for fungal growth inhibition. FEMS Microbiology Letters 69: 55-60.
3. Cao, Y-R, Wang, Q., Jin, R-X., Tang, S-K., He, W-X., Lai, H-X, Xu, L-H., and C-L Jiang. 2011. *Methylobacterium soli* sp. nov. a methanol-utilizing bacterium isolated from the forest soil. Antonie van Leeuwenhoek (2011) 99:629-634.
4. Corpe, W. A., and D. V. Basile. 1982. Methanol-utilizing bacteria associated with green plants. Devel. Industr. Microbiol. 23: 483-493.
5. Corpe, W. A., and S. Rheem. 1989. Ecology of the methylotrophic bacteria on living leaf surfaces. FEMS Microbiol. Ecol. 62: 243-250.
17
6. Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.
7. Green, P. N. 2006. *Methylobacterium*. In Dworkin, M., S. Falkow, E. Rosenberg, K.-H. Schleifer, and E. Stackebrandt (eds.). "The Prokaryotes. A Handbook on the Biology of Bacteria. Volume 5. Proteobacteria: Alpha and Beta Subclasses." Third edition. Springer, New York. Pages 257-265.
8. Holland, M. A. 1997. *Methylobacterium* and plants. Recent. Res. Devel. in Plant Physiol. 1: 207-213.

9. Holland, M. A., and J. C. Polacco. 1994. PPFMs and other covert contaminants: Is there more to plant physiology than just plant? Annu. Rev. Plant Physiol. Plant Mol. Biol. 45: 197-209.
10. Kutschera, U. 2007. Plant-associated methylobacteria as co-evolved phytosymbionts. A hypothesis. Plant Signal Behav. 2: 74-78.
11. Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.
12. Madhaiyan, M., S. Poonguzhali, H. S. Lee, K. Hari, S. P. Sundaram, and T. M. Sa. 2005. Pink-pigmented facultative methylotrophic bacteria accelerate germination, growth and yield of sugarcane clone Co86032 (*Saccharum officinarum* L.) Biol. Fertil. Soils 41: 350-358.
13. Madhaiyan, M., S. Poonguzhali, M. Senthilkumar, S. Seshadri, H. Chung, J. Yang, S. Sundaram, and T. Sa. 2004. Growth promotion and induction of systemic resistance in rice cultivar CO-47 (*Oryza sativa* L.) by *Methylobacterium* spp. Bot. Bull. Acad. Sin. 45: 315-324.
14. Madhaiyan, M., S. Poonguzhali, and T. Sa. 2007. Influence of plant species and environmental conditions on epiphytic and endophytic pink-pigmented facultative methylotrophic bacterial populations associated with field-grown rice cultivars. J Microbiol Biotechnol. 2007 October; 17(10):1645-54.
15. Stanier, R. Y., N. J. Palleroni, and M. Doudoroff. 1966. The aerobic pseudomonads: A taxonomic study. J. Gen. Microbiol. 43: 159-271.
16. Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Methylobacterium* Bacteria Nodulate and Fix Nitrogen in Symbiosis with Legumes. Jour. Bacteriol. 183(1):214-220,
17. Sy, A., A. C. J. Timmers, C. Knief, and J. A. Vorholt. 2005. Methylotrophic metabolism is advantageous for *Methylobacterium extorquens* during colonization of *Medicago truncatula* under competitive conditions. Appl. Environ. Microbiol. 71: 7245-7252.
18. Vogel, H. J., and D. M. Bonner. 1956. Acetylornithinase of *Escherichia coli*: Partial purification and some properties. J. Biol. Chem. 218: 97-106.
19. Vogel, H. J. 1956. A convenient growth medium for *Neurospora* (Medium N). Microbial Genet Bull 13: 42-43
20. Whittenbury, R., S. L. Davies, and J. F. Wilkinson. 1970. Enrichment, isolation and some properties of methane-utilizing bacteria. J. Gen. Microbiol. 61: 205-218.
21. Vuilleumier S, Chistoserdova L, Lee M C, Bringel F, Lajus A, Zhou Y, Gourion B, Barbe V, Chang J, Cruveiller S, Dossat C, Gillett W, Gruffaz C, Haugen E, Hourcade E, Levy R, Mangenot S, Muller E, Nadalig T, Pagni M, Penny C, Peyraud R, Robinson D G, Roche D, Rouy Z, Saenampechek C, Salvignol G, Vallenet D, Wu Z, Marx C J, Vorholt J A, Olson M V, Kaul R, Weissenbach J, Medigue C, Lidstrom M E. *Methylobacterium* genome sequences: a reference blueprint to investigate microbial metabolism of C1 compounds from natural and industrial sources. PLoS One. 2009; 4(5):e5584.doi: 10.1371/journal.pone.0005584. Epub 2009 May 18. PubMed PMID: 19440302; PubMed Central PMCID: PMC2680597.
22. Marx C J, Bringel F, Chistoserdova L, Moulin L, Farhan U I Haque M, Fleischman D E, Gruffaz C, Jourand P, Knief C, Lee M C, Muller E E, Nadalig T, Peyraud R, Roselli S, Russ L, Goodwin L A, Ivanova N, Kyrpides N, Lajus A, Land M L, Medigue C, Mikhailova N, Nolan M, Woyke T, Stolyar S, Vorholt J A, Vuilleumier S. Complete genome sequences of six strains of the genus *Methylobacterium*. J Bacteriol. 2012 September; 194(17):4746-8. doi: 10.1128/JB.01009-12. PubMed PMID: 22887658; PubMed Central PMCID: PMC3415506.
23. Knief C, Frances L, Vorholt J A. Competitiveness of diverse *Methylobacterium* strains in the phyllosphere of *Arabidopsis thaliana* and identification of representative models, including *M. extorquens* PA1. Microb Ecol. 2010 August; 60(2):440-52. doi: 10.1007/s00248-010-9725-3. Epub 2010 Aug. 11. PubMed PMID: 20700590.

The inclusion of various references herein is not to be construed as any admission by the Applicants that the references constitute prior art. Applicants expressly reserve their right to challenge any allegations of unpatentability of inventions disclosed herein over the references included herein.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11147276B2). An electronic copy of the "Sequence Listing" will also be available from the USPTO upon request and payment of the fee set forth in 37 CFR 1.19(b)(3).

What is claimed is:

1. A tomato plant, tomato plant part or tomato seed that is coated or partially coated with a composition comprising *Methylobacterium* strain NLS0089 which has been deposited under NRRL B-50933, wherein the composition is a solid composition comprising the *Methylobacterium* at a titer of at least $1\times10^6$ CFU/gm, or a liquid composition comprising the *Methylobacterium* at a titer of at least $1\times10^6$ CFU/mL, and wherein said composition further comprises an agriculturally acceptable adjuvant and/or excipient.

2. The tomato plant, plant part, or seed of claim 1, wherein said composition further comprises a population of one or more plant beneficial microorganisms other than *Methylobacterium*.

3. The plant, plant part, or seed of claim 1, wherein said agriculturally acceptable adjuvant is a wetter, a sticker, a penetrant, an extender, or a humectant that enhances product efficacy or ease of product application.

4. The tomato plant, plant part, or seed of claim 1, wherein said composition further comprises a pesticide.

5. The tomato plant, plant part, or seed of claim 4, wherein said pesticide is an insecticide, a fungicide, a nematocide or a bacteriocide.

6. The tomato plant, plant part, or seed of claim 4, wherein said pesticide does not substantially inhibit growth of the *Methylobacterium* by more than 50% when the composition is applied to a plant or plant part in comparison to when a composition lacking the pesticide is applied to a plant or plant part.

7. The tomato plant, plant part, or seed of claim 3, wherein said sticker comprises a polyvinyl acetate polymer or copolymer, polyvinylpyrrolidone-vinyl acetate polymer or copolymer, polyvinyl alcohol polymer or copolymer, latex polymer, alginate, acrylic copolymer, or acrylamide polymer or copolymer.

8. The tomato plant, plant part, or seed of claim 1, wherein said adjuvant comprises a surfactant, dispersant, anticaking-agent, foam-control agent, or a dye.

9. The tomato plant, plant part, or seed of claim 1, wherein said composition provides for increased fruit.

10. The tomato plant, plant part or seed of claim 1, wherein said fermentation product comprises a solid substance with adherent *Methylobacterium* grown thereon, or an emulsion with *Methylobacterium* grown therein.

11. The tomato plant, plant part, or seed of claim 1, wherein said agriculturally acceptable adjuvant is an alginate, talc, kaolin, dextrin, malto-dextrin, polysaccharide, fat, oil, protein, or gum.

12. The tomato plant, plant part, or seed of claim 1, wherein said composition is an essentially dry product having 5% or less water content, a mixture of the composition with an emulsion, or a suspension.

13. A method for improving tomato production, said method comprising: (i) treating a tomato plant, a part thereof, or a tomato seed by spraying, coating, partially coating, immersing, and/or imbibing the plant, plant part or seed with a composition comprising *Methylobacterium* strain NLS0089 which has been deposited under NRRL B-50933, wherein the composition has a *Methylobacterium* NLS0089 titer of at least $1\times10^6$ colony forming units per gram (CFU/gm) or at least $1\times10^6$ CFU per milliliter (CFU/mL); and (ii) growing the treated tomato plant, plant part, or the treated seed to produce a plant; wherein said tomato plant or tomato plant grown from said seed exhibits increased fruit production when compared to an untreated control tomato plant or a control tomato plant grown from an untreated seed, thereby improving tomato production.

14. The method of claim 13, wherein said composition comprises *Methylobacterium* at a titer of about $1\times10^6$ CFU/gm to about $1\times10^{14}$ CFU/gm for a solid composition or at a titer of about $1\times10^6$ CFU/mL to about $1\times10^{11}$ CFU/mL for a liquid composition.

15. The method of claim 13, wherein said composition partially coats said tomato plant or a part thereof, or said seed, wherein said partial coating is at least about 5%, 10%, 20%, 30%, 40%, 50%, 60%, 70%, 80%, 90%, 95%, 98%, 99%, or about 99.5% of the surface area of the tomato plant, part or seed.

16. The method of claim 13, wherein the method further comprises: (iii) harvesting seedlings, rootstock, scions, fruit, or seed from said tomato plant or tomato plant grown from said seed.

17. The method of claim 13, wherein the composition comprises an agriculturally acceptable adjuvant and/or excipient.

18. The method of claim 13, wherein said composition is applied to said tomato plant, part thereof, or seed in a hydroponic solution.

19. The method of claim 13, wherein said composition is depleted of substances that promote growth of resident microorganisms on said plant or seed.

* * * * *